United States Patent
Fouquet et al.

(10) Patent No.: US 9,710,903 B2
(45) Date of Patent: Jul. 18, 2017

(54) SYSTEM AND METHOD FOR DETECTING DESIGN AND PROCESS DEFECTS ON A WAFER USING PROCESS MONITORING FEATURES

(75) Inventors: Christophe Fouquet, Sunnyvale, CA (US); Zain Saidin, San Mateo, CA (US); Sergio Edelstein, Boston, MA (US); Savitha Nanjangud, San Jose, CA (US); Carl Hess, Los Altos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 1289 days.

(21) Appl. No.: 12/997,855

(22) PCT Filed: Jun. 5, 2009

(86) PCT No.: PCT/US2009/046379
§ 371 (c)(1),
(2), (4) Date: Jul. 28, 2011

(87) PCT Pub. No.: WO2009/152046
PCT Pub. Date: Dec. 17, 2009

(65) Prior Publication Data
US 2011/0276935 A1    Nov. 10, 2011

Related U.S. Application Data

(60) Provisional application No. 61/060,554, filed on Jun. 11, 2008.

(51) Int. Cl.
*G06F 17/50* (2006.01)
*H01L 21/66* (2006.01)
(Continued)

(52) U.S. Cl.
CPC ........ *G06T 7/0006* (2013.01); *G06F 17/5081* (2013.01); *H01L 22/12* (2013.01);
(Continued)

(58) Field of Classification Search
CPC ........ G03F 7/705; G03F 1/84; G06F 17/5081; G05B 2219/45031; G06T 7/0006; H01L 22/12
(Continued)

(56) References Cited

U.S. PATENT DOCUMENTS 6,020,957 A    2/2000  Rosengaus et al.
6,222,936 B1   4/2001  Phan et al.
(Continued)

FOREIGN PATENT DOCUMENTS

JP    8-250560        9/1996
JP    2005-209645     8/2005
(Continued)

OTHER PUBLICATIONS

Office Action for Japanese Patent Application No. 2011-513590 mailed Feb. 3, 2015.
(Continued)

*Primary Examiner* — Stacy Whitmore
(74) *Attorney, Agent, or Firm* — Ann Marie Mewherter

(57) ABSTRACT

Various systems and methods for detecting design and process defects on a wafer, reviewing defects on a wafer, selecting one or more features within a design for use as process monitoring features, or some combination thereof are provided. One system is configured to detect design defects and process defects at locations on a wafer at which images are acquired by an electron beam review subsystem based on defects in a design, additional defects in the design, which are detected by comparing an image of a die in the design printed on the wafer acquired by the electron beam review subsystem to an image of the die stored in a database, and defects detected on the wafer by a wafer inspection system.

50 Claims, 5 Drawing Sheets

(51) Int. Cl.
  *G06T 7/00* (2017.01)
  *G03F 7/20* (2006.01)
  *G01N 21/956* (2006.01)

(52) U.S. Cl.
  CPC ............ *G01N 21/956* (2013.01); *G03F 7/705* (2013.01); *G06T 2207/10061* (2013.01); *G06T 2207/30148* (2013.01); *H01L 2924/0002* (2013.01)

(58) Field of Classification Search
  USPC ........ 716/51–52, 54; 700/121; 382/144–145, 382/149
  See application file for complete search history.

(56) References Cited

U.S. PATENT DOCUMENTS

| | | | |
|---|---|---|---|
| 6,252,412 | B1 | 6/2001 | Talbot et al. |
| 6,268,093 | B1* | 7/2001 | Kenan et al. ............ 430/30 |
| 6,407,373 | B1 | 6/2002 | Dotan |
| 6,696,679 | B1 | 2/2004 | Graef et al. |
| 6,701,259 | B2 | 3/2004 | Dor et al. |
| 6,813,572 | B2 | 11/2004 | Satya et al. |
| 6,829,559 | B2 | 12/2004 | Bultman et al. |
| 6,880,136 | B2 | 4/2005 | Huisman et al. |
| 6,902,855 | B2 | 6/2005 | Peterson et al. |
| 7,027,143 | B1 | 4/2006 | Stokowski et al. |
| 7,077,556 | B2 | 7/2006 | Sugiura |
| 7,123,356 | B1 | 10/2006 | Stokowski et al. |
| 7,365,321 | B2 | 4/2008 | Nasser-Ghodsi et al. |
| 7,379,175 | B1* | 5/2008 | Stokowski et al. ........ 356/237.5 |
| 7,418,124 | B2 | 8/2008 | Peterson et al. |
| 7,570,796 | B2* | 8/2009 | Zafar et al. ............ 382/144 |
| 7,570,800 | B2* | 8/2009 | Lin et al. .............. 382/149 |
| 7,676,077 | B2* | 3/2010 | Kulkarni et al. .......... 382/144 |
| 7,684,049 | B2* | 3/2010 | De Groot et al. ........ 356/511 |
| 7,804,994 | B2* | 9/2010 | Adel et al. ............. 382/151 |
| 7,904,845 | B2* | 3/2011 | Fouquet et al. .......... 716/136 |
| 8,213,704 | B2* | 7/2012 | Peterson et al. .......... 382/145 |
| 2002/0113967 | A1 | 8/2002 | Nara et al. |
| 2003/0058444 | A1* | 3/2003 | Nara et al. ............. 356/394 |
| 2003/0164942 | A1 | 9/2003 | Take |
| 2004/0091142 | A1 | 5/2004 | Peterson et al. |
| 2005/0004774 | A1* | 1/2005 | Volk et al. ............. 702/108 |
| 2005/0221229 | A1 | 10/2005 | Nasser-Ghodsi et al. |
| 2006/0036979 | A1 | 2/2006 | Zurbrick et al. |
| 2006/0039598 | A1 | 2/2006 | Kim et al. |
| 2006/0051682 | A1 | 3/2006 | Hess et al. |
| 2006/0062445 | A1 | 3/2006 | Verma et al. |
| 2006/0082763 | A1 | 4/2006 | Teh et al. |
| 2006/0133661 | A1 | 6/2006 | Takeda et al. |
| 2006/0139627 | A1 | 6/2006 | Lin et al. |
| 2006/0161452 | A1 | 7/2006 | Hess et al. |
| 2006/0236294 | A1* | 10/2006 | Saidin et al. ............ 716/19 |
| 2006/0291714 | A1 | 12/2006 | Wu et al. |
| 2007/0035728 | A1 | 2/2007 | Kekare et al. |
| 2007/0156379 | A1 | 7/2007 | Kulkarni et al. |
| 2007/0200569 | A1 | 8/2007 | Watanabe et al. |
| 2007/0288219 | A1 | 12/2007 | Zafar et al. |
| 2008/0163140 | A1 | 7/2008 | Fouquet et al. |
| 2009/0016595 | A1* | 1/2009 | Peterson et al. ........... 382/144 |
| 2009/0080759 | A1 | 3/2009 | Bhaskar et al. |

FOREIGN PATENT DOCUMENTS

| | | |
|---|---|---|
| JP | 2005-311243 | 11/2005 |
| JP | 2006-58294 | 3/2006 |
| JP | 2006-85175 | 3/2006 |
| JP | 2007-513385 | 5/2007 |
| JP | 2007-519981 | 7/2007 |
| JP | 2009-516832 | 4/2009 |
| JP | 2010-522972 | 7/2010 |
| WO | 2005/057438 | 6/2005 |

OTHER PUBLICATIONS

International Search Report and Written Opinion for PCT/US2009/046379 mailed Nov. 18, 2009.
International Preliminary Report on Patentability for PCT/US2009/046379 mailed Dec. 23, 2010.
U.S. Appl. No. 10/716,757, filed Nov. 19, 2003 by Ma et al.
U.S. Appl. No. 11/154,310, filed Jun. 16, 2005 by Verma et al.
Vasek et al., "Using design intent to qualify and control lithography manufacturing," Design and Process Integration for Microelectronic Manufacturing IV, Proc. of SPIE, vol. 6156, 61561B, 2006.
Office Action for Japanese Patent Application No. 2011-513590 mailed Jan. 7, 2014.

* cited by examiner

SYSTEM AND METHOD FOR DETECTING DESIGN AND PROCESS DEFECTS ON A WAFER USING PROCESS MONITORING FEATURES

CROSS-REFERENCE TO RELATED APPLICATIONS

This application is a National Stage application of International Application No. PCT/US09/46379 filed Jun. 5, 2009, which claims priority to U.S. Provisional Application No. 61/060,554 entitled "Systems and Methods for Detecting Design and Process Defects on a Wafer, Reviewing Defects on a Wafer, Selecting One or More Features Within a Design for Use as Process Monitoring Features, or Some Combination Thereof," filed Jun. 11, 2008, which is incorporated by reference as if fully set forth herein.

BACKGROUND OF THE INVENTION

1. Field of the Invention

The present invention generally relates to systems and methods for detecting design and process defects on a wafer, reviewing defects on a wafer, selecting one or more features within a design for use as process monitoring features, or some combination thereof.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Another important part of manufacturing yield control is determining the cause of defects on wafers such that the cause of the defects can be corrected to thereby reduce the number of defects on other wafers. Often, determining the cause of defects involves identifying the defect type and other attributes of the defects such as size, shape, composition, etc. Since inspection typically only involves detecting defects on wafers and providing limited information about the defects such as location on the wafers, number of defects on the wafers, and sometimes defect size, defect review is often used to determine more information about individual defects than that which can be determined from inspection results. For instance, a defect review tool may be used to revisit defects detected on a wafer and to examine the defects further in some manner either automatically or manually.

Defect review typically involves generating additional information about defects at a higher resolution using either a high magnification optical system or a scanning electron microscope (SEM). The higher resolution data for the defects generated by defect review is more suitable for determining attributes of the defects such as profile, roughness, more accurate size information, etc. Defect analysis may also be performed using a system such as an electron dispersive x-ray spectroscopy (EDS) system. Such defect analysis may be performed to determine information such as composition of the defects. Attributes of the defects determined by inspection, review, analysis, or some combination thereof can be used to identify the type of the defect (i.e., defect classification) and possibly a root cause of the defects. This information can then be used to monitor and alter one or more parameters of one or more semiconductor fabrication processes to reduce or eliminate the defects.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate all of the defects may be difficult and expensive. As such, determining which of the defects actually have an effect on the electrical parameters of the devices and the yield may allow process control methods to be focused on those defects while largely ignoring others. Furthermore, at smaller design rules, process induced failures may, in some cases, tend to be systematic. That is, process induced failures tend to fail at predetermined design patterns often repeated many times within the design. Elimination of spatially systematic, electrically relevant defects is important because eliminating such defects can have a significant overall impact on yield.

Accordingly, it may be advantageous to develop systems and methods for detecting design and process defects on a wafer and/or reviewing defects on a wafer such that defects from various sources can be detected, reviewed, and analyzed using a single system or method and to develop systems and methods for selecting one or more features within a design for use as process monitoring features that provide an earlier indication of a process deviation than currently used process monitoring features.

SUMMARY OF THE INVENTION

The following description of various embodiments of systems and methods is not to be construed in any way as limiting the subject matter of the appended claims.

One embodiment relates to a system configured to detect design and process defects on a wafer. The system includes an electron beam review subsystem configured to acquire images for a wafer on which a design is printed using a manufacturing process. The system also includes a computer subsystem configured to inspect the design to detect defects in the design. The computer subsystem is also configured to compare an image of a die in the design printed on the wafer acquired by the electron beam review subsystem to an image of the die stored in a database to detect additional defects in the design. In addition, the computer subsystem is configured to determine locations on the wafer at which the images are to be acquired by the electron beam review subsystem based on the defects in the design, the additional defects in the design, and defects detected on the wafer by a wafer inspection system. The computer subsystem is further configured to use the images acquired at the locations to detect design defects and process defects at the locations.

The system described above may be farther configured according to any other embodiment(s) described herein. In addition, the system described above may be configured to perform any step(s) of any method embodiment(s) described herein.

Another embodiment relates to a system configured to review defects on a wafer. The system includes an electron beam review subsystem configured to acquire images for discrete locations on a wafer on which a design is printed using a manufacturing process. The system also includes a computer subsystem configured to determine the discrete locations based on results of PWQ analysis and to perform defect review at the discrete locations using the images acquired for the discrete locations by the electron beam review subsystem.

The system described above may be further configured according to any other embodiment(s) described herein. In addition, the system described above may be configured to perform any step(s) of any method embodiment(s) described herein.

An additional embodiment relates to a system configured to review defects on a wafer. The system includes an electron beam review subsystem configured to acquire images for discrete locations on a wafer on which a design is printed using a lithography process performed with a reticle. The system also includes a computer subsystem configured to determine the discrete locations based on results of inspection of the reticle and to perform defect review at the discrete locations using the images acquired for the discrete locations by the electron beam review subsystem, the results of the inspection of the reticle, and classification of defects detected on the reticle.

The system described above may be further configured according to any other embodiment(s) described herein. In addition, the system described above may be configured to perform any step(s) of any method embodiment(s) described herein.

A further embodiment relates to a computer-implemented method for selecting one or more features within a design for use as process monitoring features. The method includes simulating how features in a design will print on a wafer at different values of one or more parameters of a lithography process. The different values include nominal values corresponding to a center of a process window of the lithography process. The method also includes determining values of the one or more parameters at which the features will fail. In addition, the method includes identifying one or more of the features that will fail at the values closest to the nominal values. The method further includes selecting the one or more identified features as the features to be used for monitoring the lithography process. The method steps described above are performed using a computer system.

Each of the steps of the method described above may be further performed as described herein. In addition, the method described above may include any other step(s) of any other method(s) described herein. Furthermore, the method described above may be performed by any of the systems described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
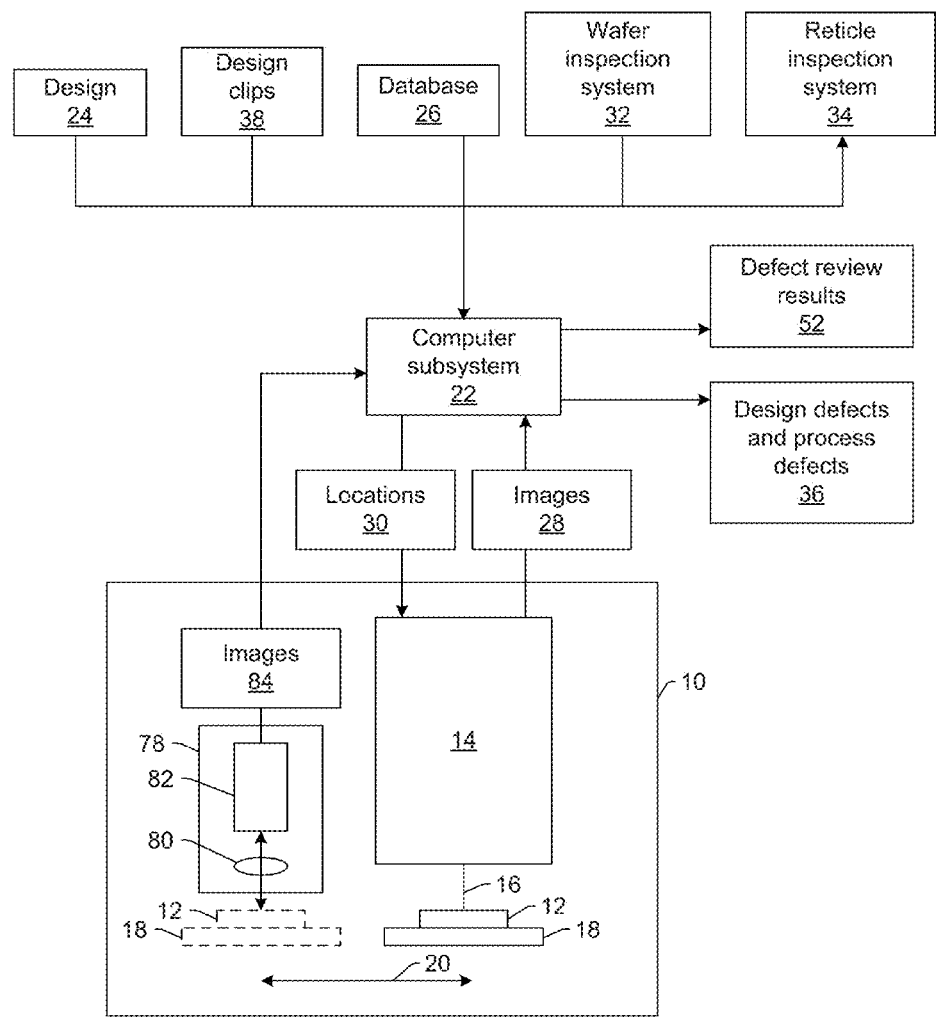
FIG. 1 is a block diagram illustrating various embodiments of a system configured to detect design and process defects on a wafer and various embodiments of a system configured to review defects on a wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The term "design" as used herein generally refers to the physical design (layout) of an IC and data derived from the physical design through complex simulation or simple geometric and Boolean operations. The design may include not only layout information, but electrical and material design information as well. Basically, the design may include any design information that is used in the creation of a "device." In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. patent application Ser. No. 11/561,735 by Kulkarni et al., published as U.S. Patent Application Publication No. 2007/0156379 on Jul. 5, 2007, now U.S. Pat. No. 7,676,077 issued on Mar. 9, 2010, and Ser. No. 11/561,659 by Zafar et al., published as U.S. Patent Application Publication No. 2007/0288219 on Dec. 13, 2007, now U.S. Pat. No. 7,570,796 issued on Aug. 4, 2009, both of which were filed on Nov. 20, 2006 and which are incorporated by reference as if fully set forth herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a system configured to detect design and process defects on a wafer. The system includes an electron beam review subsystem configured to acquire images for a wafer on which a design is printed using a manufacturing process. For example, as shown in FIG. 1, the system may include electron beam review subsystem 10 configured to acquire images for wafer 12 on which a design is printed using a manufacturing process. The manufacturing process used to print the design on the wafer may include a lithography process. The lithography process may be performed as described further herein (e.g., using a reticle). However, the manufacturing process used to print the design on the wafer may include any other semiconductor manufacturing process or processes that can print a design on a wafer such as an etch process or a combination of a lithography process and an etch process.

Electron beam review subsystem 10 includes electron column 14 configured to focus electrons 16 onto wafer 12 and to form an image of the electrons returned from the wafer. Suitable configurations of an electron column are generally known in the art. Therefore, the configuration of the electron column will not be discussed further herein for the sake of brevity. In addition, the electron column included in the electron beam review subsystem may include an electron column included in a commercially available electron beam defect review system such as the DR-5xxx systems that are commercially available from KLA-Tencor, San Jose, Calif. Alternatively, the electron column may be designed from scratch as a completely new electron column. In addition, the electron beam review subsystem may be configured as a scanning electron microscope (SEM). The images that are acquired for the wafer by the electron beam review subsystem may include any images that can be acquired for wafers by electron beam review subsystems. In addition, the images may be acquired for the wafer by the electron beam review subsystem in any suitable manner.

The electron beam review subsystem also includes stage 18 on which wafer 12 is disposed during imaging by the electron beam review subsystem. Stage 18 may include any suitable chuck, wafer handler, or mechanical and/or robotic assembly known in the art. The stage may also be configured to move and/or position the wafer in any suitable manner known in the art. For example, stage 18 may be configured to move the wafer in directions shown by arrow 20.

Since the system includes an electron beam review subsystem, the system may be configured essentially as a defect review system. However, as described further herein, the system embodiments are configured to have capabilities not typically provided on a defect review system. For example, the system also includes computer subsystem 22 configured to inspect design 24 to detect defects in the design. In this manner, the system is configured for integrated design scan capability on an electron beam review system.

The computer subsystem may be configured to inspect the design in a number of different ways. For example, at the design phase, resolution enhancement technology (RET) features such as optical proximity correction (OPC) features may be added to the design, and the computer subsystem may be configured to inspect the "decorated" design. In this manner, the computer subsystem may be configured to inspect the design after RET and/or OPC features have been added to the design. Output of the design inspection performed by the computer subsystem may include, for example, hot spots, design defects, and other results of design inspection known in the art.

Design 24 may have any suitable form known in the art. For example, the design may be stored in a graphical data stream (GDS) file, any other standard machine-readable file, any other suitable file known in the art, or a design database. The term "GDS" as used herein generally refers to the geometrical design layout information and can be any representation of that data. Such a representation will commonly be in either GDSII or OASIS format, but may alternatively be in any other suitable representation. For example, a GDSII file is one of a class of files used for the representation of design layout data. Other examples of such files include GL1 and OASIS files. All such representations may be used in the embodiments as described herein with respect to GDS and GDSII.

The computer subsystem may be configured to inspect the design (decorated or not) using any suitable design inspection method or technique known in the art. Examples of methods for design inspection that may be performed by the computer subsystem are illustrated in commonly owned U.S. patent application Ser. No. 11/003,291 by Hess et al. filed Dec. 3, 2004, which published as U.S. Patent Application Publication No. 2006/0051682 on Mar. 9, 2006, now U.S. Pat. No. 8,151,220 issued on Apr. 3, 2010, Ser. No. 11/048,630 by Saidin et al. filed Jan. 31, 2005, which published as U.S. Patent Application Publication No. 2006/0236294 on Oct. 19, 2006, now U.S. Pat. No. 7,646,906 issued on Jan. 12, 2010, and Ser. No. 11/226,698 by Verma et al. filed Sep. 14, 2005, which published as U.S. Patent Application Publication No. 2006/0062445 on Mar. 23, 2006, now U.S. Pat. No. 7,689,966 on Mar. 30, 2010, all of which are incorporated by reference as if fully set forth herein. The embodiments described herein may include or be configured to perform any step(s) of any method(s) described in these patent applications.

In one embodiment, the computer subsystem is configured to alter the design to correct the defects in the design. Altering the design may include altering one or more characteristics of RET in the design since changing the RET in the design may alter how the features in the design are printed on the wafer thereby possibly eliminating defects in the design without fundamentally changing the function of the device. In one such example, one or more characteristics (e.g., size, shape, placement) of one or more RET may be altered based on the defects detected in the design (e.g., using a rules database or other data structure that relates one or more characteristics of RET to how the RET affect printing of features). The portion of the design in which the RET were altered (or the entire design) may then be re-inspected as described above to determine if the changes in the RET eliminated the defect(s) from the design. In this manner, the design may be altered and re-inspected in an iterative manner until the design is defect-free or determined to contain only tolerable defects. In a similar manner, one or more characteristics of one or more non-RET features in the design may be altered to eliminate defects from the design.

The computer subsystem may also be configured to simulate reticle layout data such that if a reticle is fabricated with the reticle layout data and the reticle is used to fabricate the wafer, a predetermined device pattern will be formed on the wafer after an etch process as described in commonly assigned U.S. patent application Ser. No. 11/154,310 by Verma et al. filed Jun. 16, 2005, now abandoned, which is incorporated by reference as if fully set forth herein. In other words, the computer subsystem may perform simulations to create a design based on the desired device pattern to be formed on a wafer. The computer subsystem described herein may be configured to perform any step(s) of any method(s) described in this patent application. The computer subsystem may also be configured to use such methods and systems to correct the defects in the design.

Computer subsystem 22 is also configured to compare an image of a die in the design printed on wafer 12 acquired by electron beam review subsystem 10 to an image of the die stored in database 26 to detect additional defects in design 24. In this manner, the embodiments described herein are also configured for integrated die-to-database capability (with design scan capability as described above) on an electron beam review system. For example, a reticle may be fabricated using or based on the design (altered or not) using any suitable reticle manufacturing process or processes. The reticle may then be used to print a die on the wafer. An image of a die (or a portion of the die) in the design printed on the wafer may be acquired by the electron beam review subsystem as described further herein.

Images 28 generated by electron column 14 of electron beam review subsystem 10 may be provided to the computer subsystem by the electron beam review subsystem. In one such example, a detector (not shown) of the electron column may be coupled to the computer subsystem by one or more transmission media (not shown), which may include any suitable transmission media known in the art including "wired" and/or "wireless" transmission media such that the computer subsystem can receive images generated by the detector. The computer subsystem may acquire an image of the die stored in database 26 in any suitable manner and as described further herein.

The image of the die stored in the database may be, for example, a simulated image illustrating how the die in the design would ideally be printed on the wafer or any other suitable reference image of the die. The computer subsystem may compare the image of the die acquired by the electron beam review subsystem to the image of the die stored in the database in any suitable manner. In general, any differences between the image of the die acquired by the electron beam review subsystem and the image of the die stored in the database may be determined by the computer subsystem to be additional defects in the design. However, the computer subsystem may be configured to use any suitable defect detection algorithm to detect the additional defects in the design based on the comparison of the image of the die acquired by the electron beam review subsystem and the image of the die stored in the database.

In one embodiment, the additional defects in the design (detected in a die-to-database manner as described above) were not detected by the inspection of the design performed by the computer subsystem. In this manner, the system embodiments described herein are capable of performing die-to-database inspection to locate design defects that were not identified by design inspection (design scan). For example, the die-to-database design inspection may detect different defects in the design than the inspection performed without printing the design on the wafer. However, the die-to-database design inspection may also detect some of the same defects in the design that are detected by the inspection performed without printing the design on the wafer. The computer subsystem may be configured to determine the positions of the additional defects in design data space (based on their wafer space positions) such that the additional defects can be compared to the other design defects. In this manner, defects detected in the design in different manners can be compared on a location basis (a design space location basis or a wafer space location basis if the positions of the design defects detected without printing the design on the wafer are determined in wafer space based on their design space positions)) to determine which defects were detected by both of the inspections and which defects were detected by only one of the inspections. The positions of defects in wafer space may be translated to design data space positions as described in the above-referenced patent applications by Kulkarni et al. and Zafar et al. The embodiments described herein may be configured to perform any step(s) of any method(s) described in these patent applications.

The computer subsystem is also configured to determine locations 30 on wafer 12 at which images 28 are to be acquired by electron beam review subsystem 10 based on the defects in the design, the additional defects in the design, and defects detected on the wafer by wafer inspection system 32. The computer subsystem may be configured to determine the locations on the wafer at which the images are to be acquired by determining coordinates of the locations on the wafer. For example, the computer subsystem may be configured to determine the coordinates of the locations on the wafer to be imaged by translating design defect coordinates and additional design defect coordinates into wafer coordinates for imaging by the electron beam review subsystem. Translating the coordinates may be performed based on the coordinates of the defects and additional defects in the design determined by the computer subsystem and additional information such as the layout of the design on the wafer and/or the layout in which the reticle will be printed on the wafer. In this manner, the computer subsystem may be configured to translate coordinates determined in a space other than wafer space (e.g., design space) into coordinates in wafer space. Such translation of coordinates may be further performed as described in the above-referenced patent applications by Kulkarni et al. and Zafar et al. In addition, translating the coordinates may include translating coordinates determined by one or more inspections into coordinates in a format useable by the defect review system or the electron beam review subsystem.

The wafer inspection system may be used to inspect a wafer after wafer processing. For example, during the wafer processing phase, which may include wafer processing such as lithography, etch, deposition, chemical-mechanical polishing (CMP), etc., a wafer inspection system may be used to inspect wafers that have been processed. Output of the wafer inspection system includes information about process defects (e.g., information about defects detected on the wafers that have been processed or defects that are caused by the wafer processing). The wafer inspection system may include any appropriate wafer inspection system known in the art such as the 23xx series tools, 28xx series tools, AIT tools, Puma 9000 series tools, and Puma 91xx series tools, which are commercially available from KLA-Tencor.

In one embodiment, the computer subsystem is configured to acquire information about the defects detected on the wafer by wafer inspection system 32 from output generated by the wafer inspection system. The information may include, for example, coordinates of defects detected by the wafer inspection system. In this manner, coordinates of defects detected on the wafer may be provided by a wafer inspection system. Acquiring the information about the defects may include requesting the information or data structure(s) such as file(s) containing the information from the wafer inspection system or other system(s) in which the wafer inspection system stored data structure(s) containing the information about the defects. Acquiring the information about the defects may also or alternatively include retrieving the information or data structure(s) such as file(s) containing the information from one or more storage media in which the information or the data structure(s) were stored (e.g., by the wafer inspection system). The one or more storage media may include individual storage media of the wafer inspection system or one or more other storage media coupled to the wafer inspection system (e.g., a fab database). The output of the wafer inspection system acquired by the computer subsystem may be acquired in any suitable format such as a KLARF file. Alternatively, coordinates of defects detected on the wafer may be provided to the computer subsystem by a user of the system.

In this manner, the computer subsystem may be connected to the wafer inspection system (and optionally other inspection systems described herein), other system(s) (e.g., systems other than inspection systems), or one or more storage media in a manner such that the computer subsystem can acquire the information about the defects detected on the wafer. The computer subsystem may be connected to the wafer inspection system in any suitable manner (e.g., by one or more transmission media that serve as data link(s) across which the computer subsystem can receive the information about the defects). In addition, the computer subsystem may include any suitable architecture that can be used to connect with all relevant systems (e.g., one or more wafer inspection systems, one or more reticle inspection systems, one or more process window qualification (PWQ) inspection systems, one or more other systems described herein, etc.). The computer subsystem may be connected to each of these other systems using closed format technology such as that commercially available from KLA-Tencor. In addition, the computer subsystem may be coupled to the systems described herein such that the computer subsystem can receive output from any of the systems and send output to any of the systems. Therefore, as described further herein, the unique value of various inspection systems and the output of the inspection systems may be extended to defect review systems by extending the connectivity of the systems.

The computer subsystem may be configured to determine the locations on the wafer at which the images are to be acquired based on the defects detected on the wafer such that both systematic and random process defects will be imaged by the electron beam review subsystem. For example, the computer subsystem may be configured to perform systematic defect extraction using output generated by wafer inspection. In this manner, the computer subsystem may be configured to separate systematic defects from random defects in a population of defects detected by wafer inspection. Extraction of the systematic defects may be performed by design-based binning (DBB) or using design information for the defects detected on the wafer. Such systematic defect extraction and DBB may be performed as described in the above-referenced patent applications by Kulkarni et al. and Zafar et al. In addition, the embodiments may be configured to perform detection methods for systematic defects utilizing design information and critical dimension (CD) measurements, possibly in combination with any of the other information described herein.

After the systematic process defects have been separated from the random process defects, each sub-population of defects may be separately sampled (i.e., selected for imaging). In this manner, the defects for which images are to be acquired by the electron beam review subsystem may be separately selected from the systematic process defects and the random process defects thereby effectively determining the locations on the wafer (corresponding to the selected defects) at which the images are to be acquired. The defects to be imaged may be selected from the random process defect sub-population in any suitable manner random sampling). The defects in the systematic process defect sub-population to be imaged may be selected based on additional information about the systematic process defects. For instance, at least some systematic defects located in different portions of the design may be selected, or systematic defects located in certain (e.g., yield relevant) portions of the design may be selected more heavily than systematic defects located in other portions of the design.

In a similar manner, the computer subsystem may be configured to perform design-based classification (DBC) to filter defects from the population detected, by wafer inspection prior to determining the locations on the wafer at which the images are to be acquired. For example, the computer subsystem may be configured to extract design clips for defects detected on the wafer. Extracting the design clips may be performed as described in the above-referenced patent applications by Kulkarni et al. and Zafar et al. The extracted design clips for the detected defects may be compared to a data structure that includes design clips for patterns of interest (POI). The data structure may be referred to as a DBC library, and the POI may be defined by a user. In this manner, the DBC library may include different POI associated with different DBC bins. The computer subsystem may be configured to compare the design clips extracted for the defects detected on the wafer to the design clips in the DBC library.

Results of the comparison may be used to assign DBC bins to the defects detected on the wafer. For example, if an extracted design clip matches a design clip in the DBC library, the defect for which the design clip was extracted may be assigned the DBC bin corresponding to the matching design clip in the DBC library. If the extracted design clip does not match any of the design clips in the DBC library, the defect for which the design clip was extracted may be assigned a DBC bin corresponding to an empty GDS clip (or a dummy filter) since the design clip does not correspond to any of the POI in the DBC library. Such defects may then be filtered from the defect population prior to sampling of the defect population. DBC may be further performed as described in the above-referenced patent applications by Kulkarni et al. and Zafar et al.

In this manner, in preparation for sampling defects detected on the wafer, the computer subsystem may be configured to perform DBC to "bin out" systematic defects or nuisance. Performing DBC will also remove defects that fall on dummy fill structures or known non-POI. In this manner, preparation for a sampling plan may include binning out "dummy fill" defects by DBC and binning out defects in known non-POI. Binning out dummy fill defects may remove a substantial number of the defects in a population prior to sampling the defect population. Removing such defects prior to sampling is advantageous since the user generally does not care about such defects and such defects have no affect on yield. In addition, preparation for the sample plan may include identifying defects located within a known POI. Identifying the defects within a known POI may be performed using a data structure created as described herein, which may be configured as a library of POI generated by discrete defect review (DDR), which may be performed as described further herein.

However, the computer subsystem may be configured to determine the locations on the wafer at which the images are to be acquired based on the defects detected on the wafer without regard to whether the defects are systematic process defects or random process defects. For example, the computer subsystem may be configured to select defects for imaging from the entire population of the defects detected by wafer inspection. The coordinates of the selected defects are then the coordinates of the locations on the wafer at which the images are to be acquired. The computer subsystem may also apply some correction or translation to the coordinates determined by wafer inspection such that the coordinates are referenced to or can be used by the electron beam review subsystem. The defects may be selected from the entire defect population in any suitable manner. The computer subsystem may use the images acquired for the locations determined based on the selected locations as described further herein to determine if the process defects are systematic process defects or random process defects.

The computer subsystem may be configured to determine the coordinates of the locations on the wafer to be imaged by the electron beam review subsystem as a single set of coordinates. For example, determining the coordinates may include combining several sources of coordinates into one single source of coordinates that will constitute the sample for imaging by the electron beam review subsystem. For example, the computer subsystem is configured to identify the locations of potential design and/or process defects using the output of the integrated design scan capability, die-to-database design inspection capability, and wafer inspection system defect files. Determining the coordinates may include using multiple files to combine the defect coordinates into one single source of defect coordinates. The multiple sources of defect coordinates that are combined may include any other sources described herein. For example, the multiple sources of defect coordinates may also include output from reticle inspection and PWQ analysis. The system may also be configured to have flexibility such that the user can select the sources of defect coordinates. In some embodiments, the computer subsystem is configured to create a file that includes information about the locations at which the images are to be acquired by the electron beam review subsystem. For example, the file may include information to enable the electron beam review subsystem to "drive" substantially accurately to a potential defect location to capture an image of the defect.

In one embodiment, the computer subsystem is configured to identify hot spots in the design and to determine the locations on the wafer at which the images are to be acquired by the electron beam review subsystem based on the hot spots in the design. The hot spots in the design may be identified by inspection of the design performed by the computer subsystem as described above. However, other or additional hot spots may be identified by the computer subsystem in any other suitable manner. For example, the computer subsystem may identify hot spots in the design by performing design rule checking (DRC) to produce a list of critical points in the design. DRC is commonly performed for quality control of reticle layout data prior to reticle manufacturing. Thus, DRC may not produce hot spots. Instead, the results of DRC may be used to identify new marginal hot spots that were either in the design manual but not part of DRC rules or are newly discovered. In addition, the computer subsystem may identify hot spots using electronic design automation (EDA). The computer subsystem may also use design rules (DRC used as a marginality checker) and EDA to identify hot spots. Furthermore, the hot spots may be identified using technology for computer-aided design (TCAD) tools and proxies. TCAD tools are commercially available from Synopsis, Inc., Mountain View, Calif. In addition, or alternatively, DesignScan analysis software that is commercially available from KLA-Tencor, arbitrary pattern searching, and design context (e.g., functional block, design library element, cell, whether a pattern is redundant or not, pattern density, dummy/fill versus active, etc.) may be used by the computer subsystem to identify hot spots. In another example, design data based grouping of defects (with or without pareto analysis) may be used to discover and group hot spots, which may be performed as described in the patent applications by Kulkarni et al. and Zafar et al. incorporated by reference above. The computer subsystem may be configured to determine the locations on the wafer at which the images are to be acquired by the electron beam review subsystem based on the hot spots according to any of the embodiments described herein (e.g., by translating design space coordinates to wafer space coordinates).

In another embodiment, the computer subsystem is configured to detect defects on a reticle using PWQ analysis and to determine the locations on the wafer at which the images are to be acquired by the electron beam review subsystem based on the defects on the reticle. PWQ analysis may include characterizing the process window (PW) that can be used with a fabricated reticle. The computer subsystem may perform PWQ analysis during a photo or lithography PW characterization phase. Results of the PWQ analysis may include lithography hot spots. The computer subsystem may be configured to perform PWQ analysis as described in commonly owned U.S. Pat. No. 6,902,855 to Peterson et al. and U.S. Pat. No. 7,418,124 to Peterson et al. and commonly owned U.S. patent application Ser. No. 11/005,658 by Wu et al. filed Dec. 7, 2004, which published as U.S. Patent Application Publication No. 2006/0291714 on Dec. 28, 2006, now U.S. Pat. No. 7,729,529 issued on Jun. 1, 2010, Ser. No. 11/314,813 by Kekare et al. filed Dec. 20, 2005, which published as U.S. Patent Application Publication No. 2007/0035728 on Feb. 15, 2007, now U.S. Pat. No. 7,769,225 issued on Aug. 3, 2010 and Ser. No. 12/116,664 by Peterson et al. filed May 7, 2008, which published as U.S. Patent Application Publication No. 2009/0016595 on Jan. 15, 2009, now U.S. Pat. No. 8,213,704 issued on Jul. 3, 2012, all of which are incorporated by reference as if fully set forth herein. The embodiments described herein may be configured to perform any step(s) of any method(s) described in these patents and patent applications. In addition, the computer subsystem may be configured to perform PWQ analysis to detect defects on the reticle using images of the reticle printed on wafers at different values of process parameters (and such images can be acquired from a wafer inspection system as described further herein). Alternatively, the computer subsystem may be configured to perform PWQ analysis by generating images that simulate how the reticle would print on wafers at different values of process parameters and detecting defects on the reticle using the simulated images. The computer subsystem may be configured to determine the locations on the wafer at which the images are to be acquired by the electron beam review subsystem based on the defects detected on the reticle using PWQ analysis according to any of the embodiments described herein (e.g., by translating reticle space coordinates to wafer space coordinates).

In an additional embodiment, the computer subsystem is configured to determine the locations on the wafer at which the images are to be acquired by the electron beam review subsystem based on defects detected on a reticle by reticle inspection system 34. For example, during the reticle fabrication phase, reticle fabrication may be performed using the design, and a reticle inspection system may be used to inspect the fabricated reticle. Output of the reticle inspection system may include, but is not limited to, reticle defects and reticle contamination. The reticle inspection system may include any suitable reticle inspection system. For example, the reticle inspection system may be a commercially available reticle inspection system such as the STARlight, STARlight-2, and TeraScan systems that are commercially available from KLA-Tencor. Additional examples of reticle inspection systems are described in commonly owned U.S. Pat. No. 7,027,143 to Stokowski et al., U.S. Pat. No.

7,123,356 to Stokowski et al., and U.S. Pat. No. 7,379,175 to Stokowski et al., all of which are incorporated by reference as if fully set forth herein. Reticle inspection system 34 may be configured as described in these patents.

The computer subsystem may also be configured to use results of reticle inspection to evaluate defects detected on the reticle. For example, the computer subsystem may be configured to generate a simulated image of a defect on a reticle using information about the defect generated by inspection of one level of the reticle in combination with information about a different level on the reticle as described in commonly owned U.S. patent application Ser. No. 11/181,358 to Zurbrick et al. filed Jul. 14, 2005, which published as U.S. Patent Application Publication No. 2006/0036979 on Feb. 16, 2006, now U.S. Pat. No. 7,788,629 issued on Aug. 31, 2010, and which is incorporated by reference as if fully set forth herein. The system embodiments described herein may be configured to perform any step(s) of any method(s) described in this patent application.

In a further embodiment, the computer subsystem is configured to determine the locations on the wafer at which the images are to be acquired by the electron beam review subsystem based on yield simulation results. For example, electrical testing results or other information about the electrical properties of a device corresponding to the design such as resistance, capacitance, timing, etc. can be used in combination with one or more attributes of the design and/or one or more attributes of the potential defects to determine which portions of the design will be most susceptible to defects that adversely affect yield of the device. The electrical testing results or other information about the electrical properties may be determined by the computer subsystem (e.g., using simulation) and/or may be acquired front another source e.g., netlist information). In this manner, portions of the design that are more likely to cause parametric issues due to defects can be identified and separated from portions of the design that are less likely or unlikely to cause parametric issues.

In this manner, the yield simulation results may indicate which portions of the design are more susceptible to affecting yield, and the computer subsystem may determine the locations on the wafer at which the images are to be acquired by the electron beam review subsystem to include locations on the wafer at which those portions of the design will be formed. As such, the images acquired for those locations can be used to monitor the locations for potential yield impacting defects, and since the images are acquired using an electron beam review subsystem, the images can be used to detect potential yield impacting defects in those locations with greater accuracy and higher sensitivity than using a wafer inspection system.

The computer subsystem may also be configured to use yield simulation results for individual defects detected on the wafer to determine which defects (and therefore locations corresponding to the defects) for which images should be acquired by the electron beam review subsystem. For example, one or more attributes of the design proximate the positions of the process defects in design data space, one or more attributes of the process defects, or some combination thereof may be used to determine the design-based potential yield impact of the process defects. In one such example, defect size and position of the defect in the design can be used to determine the likelihood that the defect will cause an electrical fault, which can then be used to indicate yield relevance of the defect. In particular, as the defect size increases and the pattern complexity increases, the likelihood that a defect will kill the die or change one or more electrical attributes of the device also increases. Therefore, a relationship describing the likelihood that a defect will kill a die or change one or more electrical attributes of the device as a function of defect size and pattern complexity may be used to determine the relative risk of each defect on each wafer. In addition, examples of methods for predicting yield are illustrated in commonly owned U.S. Pat. No. 6,813,572 to Satya et al., which is incorporated by reference as if fully set forth herein. The embodiments described herein may be configured to perform any step(s) of any method(s) described in this patent.

In this manner, the yield simulation results may indicate which process defects may have a greater impact on yield, and the computer subsystem may determine the locations on the wafer at which the images are to be acquired by the electron beam review subsystem to include locations on the wafer at which those defects are located. As such, the images acquired for those locations can be used to determine more information about the potentially yield relevant process defects.

The computer subsystem may be configured to generate any of the yield simulation results described above (by performing yield simulation) or to acquire the yield simulation results from another system. For example, the computer subsystem may perform the yield simulation for individual process defects or may acquire the yield simulation results for individual process defects from another source (e.g., a wafer inspection system having such yield simulation capability).

Therefore, the embodiments described herein perform systematic defect inspection (design inspection, die-to-database design inspection) and may have connectivity to other systematic defect inspection systems (such as reticle and lithography inspection systems). In this manner, during various phases in a fabrication process, different inspection systems may be used to detect different potential sources of systematic defects, and the results of the different inspection systems can be combined to determine locations on a wafer at which systematic defects may be located.

The computer subsystem, therefore, generates a sample of locations on a wafer to be imaged by the electron beam review subsystem. In addition, the locations on the wafer are determined as described herein such that images acquired for the locations can be used to determine if non-process defects cause defects on the wafer. For example, as described herein, the computer subsystem may translate coordinates of the design defects and the additional design defects into coordinates on the wafer. In this manner, images acquired for those locations can be used to determine if the design and additional design defects cause defects on the wafer. Therefore, at least a portion of the locations on the wafer to be imaged by the electron beam review subsystem determined as described herein constitute a potential defect sample. In this manner, the results of inspecting the design and detecting additional defects in the design may be used in combination to determine locations to be imaged by the electron beam review subsystem for defect detection purposes and/or to be imaged during DDR for systematic defects, which may be performed as described further herein.

The embodiments described herein, therefore, advantageously determine locations on a wafer for systematic defect detection and/or review. In this manner, the computer subsystem effectively creates a systematic defect inspection and review sample. For example, as described further herein, the computer subsystem may be configured to determine locations on a wafer for DDR for systematic defects. However, the computer subsystem may also advantageously determine locations on a wafer for both systematic defect review and random defect review. In addition, the systems described herein may be used to perform both systematic and random defect review. Output from the system may include results from review of both systematic and random defects.

In this manner, the system may be configured as a combined random and systematic defect review system and may include a systematic defect review module (not shown) and a random defect review module (not shown). Each of the review modules may be configured as described above with respect to electron beam review subsystem 10. A systematic defect sample and recipe (SDSR) file may be created by the computer subsystem and provided to the systematic defect review module, and output of wafer inspection such as a KLARF file may be provided to the computer subsystem and the random defect review module. For example, the computer subsystem may be configured to read traditional KLARF files for random defect review and create an SDSR file for systematic defect review, and the system may be used to perform both types of review at the same time on a wafer. In addition, a single review module (e.g., electron beam review subsystem 10) may be configured for systematic and random defect review.

For example, as described further herein, the computer subsystem may be configured to acquire results of inspection of the wafer performed by a wafer inspection system and randomly select defects detected on the wafer (from the results of wafer inspection) for review. The wafer inspection results may be acquired as described herein, and defects may be randomly selected from the wafer inspection results in any suitable manner. The locations on the wafer for which the coordinates are determined based on the design and additional design defects constitute a systematic defect sample, the randomly selected defects constitute a random sample, and imaging and other functions described herein for the systematic defect sample and the random sample may be performed in the same process. Defects randomly selected from the wafer inspection results may be reviewed by electron beam review and classification (EBRC), which may be performed by the electron beam review subsystem. In this manner, the process defects detected by the wafer inspection system may be reviewed by the system having capability similar to an EBRC system. However, the same system may be used to perform both DDR for the systematic or potential systematic defects and EBRC for the random defect sample.

Prior to imaging, if analysis of results of the wafer inspection indicates that one or more defects detected by wafer inspection are systematic defects, the computer subsystem may be configured to add the one or more defects to the systematic defect sample and if the one or more defects are included in the random sample, remove the one or more defects from the random sample. For example, analysis of the results of wafer inspection may include DBB, which may be performed by the wafer inspection system, the computer subsystem of the system embodiments described herein, another stand-alone computer system, or any other suitable system. DBB may be performed as described in the above-referenced patent applications by Kulkarni et al. and Zafar et al. DBB may be used to identify process defects that are systematic defects or potential systematic defects on the wafer using the wafer inspection results.

Therefore, if DBB determines that defects detected by wafer inspection are systematic or potential systematic defects, those defects may be added to the systematic defect sample (e.g., by combining the coordinates of those defects with the coordinates on the wafer translated from coordinates included in results of design inspection (and possibly reticle inspection, PWQ analysis, etc.) so that they are included in a single source of defect coordinates at which DDR is performed). If the defects on the wafer identified as systematic or potential systematic defects by DBB have coordinates on the wafer that are already included in the coordinates translated from results of design inspection (and possibly reticle inspection, PWQ analysis, etc.), the single source of defect coordinates may include only one instance of those coordinates such that the location on the wafer corresponding to those coordinates is reviewed only once for a systematic defect. If the defects on the wafer identified as systematic or potential systematic defects by DBB are included in the sample of defects that was randomly selected for defect review, those defects may be removed from the random defect sample such that the defects are not reviewed during EBRC. In this manner, defects or locations of potential defects will not be reviewed twice during both DDR and EBRC. DBB may also be used in combination with the wafer inspection system to identify lithography hot spots and/or to alter (e.g., correct) the lithography hot spots in results generated by PWQ analysis.

In this manner, the computer subsystem may be configured to perform dynamic sample creation for DDR and EBRC. For example, dynamic sample creation may include using the accumulated history of detected defects to create the optimum sample. In one such example, as described further herein, if a defect detected by a wafer inspection system is determined to be a systematic defect, the defect will be added to the sample for the DDR run, while being removed from the EBRC sample.

The embodiments described herein are, therefore, configured specifically for systematic defect detection and review, which may be performed in combination with defect review of other types of defects as described further herein. In contrast, currently used defect review systems and methods generally perform defect review for a sample of a population of defects detected on a specimen without regard to the type of the defects. In this manner, currently used defect review systems and methods tend to review a substantial number of random defects on the specimen since most of the defects detected on the specimen may be random defects. Such defect review may be disadvantageous since systematic defects may be more yield relevant than random defects, and, as such, more information about the systematic defects is preferably generated such that the yield can be improved based on the systematic defect information.

However, as described herein, different types of defects may be detected, the types of the detected defects may be identified, and/or the different types of defects can be separated from each other by binning. Therefore, the embodiments described herein can use such information about defect type to monitor all types of defects and monitor all types of defects together as described further herein. In addition, the system embodiments described herein can perform a number of functions that can only be performed today using a fleet of different methods and systems. Such functions include design inspection (design scan), PWQ, SEM die-to-database, and traditional EBRC methods. In this manner, the system embodiments described herein are advantageous in that they provide within one system the full capability to locate and/or classify all design and process defect types. In addition, the embodiments described herein enable the integration of information from several subsystems or systems together with enhanced software and/or algorithms to provide the user with an easy to use, stand-alone application to detect and review systematic defects. Furthermore, the embodiments described herein may be implemented by modifying an existing defect review system such as an EBRC system commercially available from KLA-Tencor or by creating an entirely new system.

In contrast, no systems that can be used for the overall set of applications described herein are currently available. Using a large number of different tools or systems to perform the functions that can be performed using the system embodiments described herein is disadvantageous for a number of obvious reasons. Some manual cumbersome step-by-step process may be used to try to perform some of the functions described herein. However, such a process would have a number of disadvantages. For example, such a process would take a substantially long time, is manual, is complicated to implement, requires extensive expertise, is not repeatable, and is therefore difficult to implement and maintain. In addition, some other functions that can be performed by the system embodiments described herein are not covered by any currently used methods or systems.

The computer subsystem may also be configured to output the locations for which the images are to be acquired to the electron beam review subsystem. For example, the coordinates of locations to be imaged may be provided to electron beam review subsystem 10 by computer subsystem 22. In one such example, the computer subsystem may be coupled or connected to the electron beam review subsystem such that the computer subsystem can send the coordinates of the locations to be imaged to the electron beam review subsystem. The images can then be acquired by the electron beam review subsystem at the coordinates of the locations determined by the computer subsystem. In this manner, the system has the capability to acquire images (e.g., SEM images) of locations corresponding to defect or hot spot locations identified by design inspection or die-to-database design inspection and the capability to acquire images (e.g., SEM images) of defects detected on a wafer.

For imaging of the locations of the wafer, several imaging modes may be available. Different imaging modes may represent different versions of the system. Examples of suitable imaging modes include relatively high resolution SEM imaging, relatively high resolution optical imaging in several optical modes, relatively high resolution tilt SEM imaging, substantially high resolution ion beam imaging, substantially high resolution transmission electron microscopy (TEM) imaging, and substantially high resolution atomic, force microscope (AFM) imaging. The system may also be configured to perform one or more measurements of features or defects at the locations. For example, using any of the imaging modes described above, measurement of features or defects may be performed using the acquired images and one or more algorithms. The system may be configured to perform profiling of the defects. For example, tilt and 3D imaging capabilities (provided, for example, by AFM or substantially high resolution imaging of a cross-section with SEM or TEM) may be used to provide a profile of a feature or defect at a location on the wafer.

Computer subsystem 22 is further configured to use images 28 acquired for locations 30 to detect design defects and process defects 36 at the locations. In one embodiment, the process defects include systematic process defects, random process defects, or a combination thereof. In this manner, the embodiments described herein provide discrete defect detection systems for locating design defects and systematic or random process defects. As such, the embodiments described herein are different than other defect detection systems in that defect detection may be performed by the embodiments described herein at only discrete locations on the wafer. In contrast, most other defect detection systems scan relatively large areas on the wafer to detect any defects that may be present in the entire scanned area. In addition, the embodiments described herein integrate within a single system the capability to locate design defects and systematic or random process defects.

In one embodiment, the computer subsystem is configured to detect the design defects and the process defects by comparing a portion of the image of the die printed on the wafer to a design clip. In this manner, the computer subsystem may be configured to perform die-to-database comparisons for potential defect locations to determine the existence of a defect using a design clip. For example, the computer subsystem may compare the acquired image to a design clip corresponding to the same location and compare any differences between the image and the design clip to a threshold to determine if the differences qualify as potential defects. However, the computer subsystem may also or alternatively be configured to detect defects at the locations by applying any other suitable defect detection algorithm and/or method to the results of the comparison between the images and the corresponding design clips.

The design clip may be acquired by the computer subsystem from design clips 38. The design clips may include any suitable design clips and may have any suitable format such as the design formats described further herein. The design clips may be created from design 24. In addition, the design clips may be stored separately from the design or in the same storage medium (e.g., database) as the design. The design clips may be extracted from the design by the computer subsystem in some instances (e.g., based on locations for which the images are acquired with respect to the design). However, the design clips may be extracted from the design by any other suitable method or system and then accessed or retrieved from a storage medium by the computer subsystem (e.g., based on the locations for which the images are acquired with respect to the design and/or based on portions of the design that appear in the images).

The embodiments described herein, therefore, include a defect review subsystem (the electron beam review subsystem) and are configured to perform defect detection at discrete locations on a wafer using images acquired for the locations by the defect review subsystem to essentially inspect those locations for design and process defects. For example, as described further herein, the locations on the wafer determined by the computer subsystem at which images are to be acquired include locations that correspond to defects in a design and may also include locations that correspond to hot spots, defects detected on a reticle, defects on the reticle detected by PWQ analysis, or some combination thereof. In this manner, the system embodiments described herein have the ability to acquire SEM images of potential defect locations identified by design simulation/inspection, yield simulation, reticle inspection systems, and PWQ analysis. As such, the locations on the wafer at which the computer subsystem determines that images are to be acquired correspond to defects (not-wafer defects) that may produce systematic defects on a wafer.

In addition, those discrete locations on the wafer may be inspected using the electron beam review subsystem regardless of whether or not defects were detected at those discrete locations by inspection of the wafer. Instead, those locations are inspected using the electron beam review subsystem to determine if a potential systematic defect causing mechanism in a design (or other systematic defect causing mechanism, e.g., a reticle) has caused systematic defects on the wafer. For example, the computer subsystem may be configured to use images acquired for the locations by the electron beam review subsystem to determine if the design defects and additional design defects cause systematic defects on the wafer. As such, in embodiments described herein, a defect review system may essentially be used for discrete inspection of a wafer for in-line monitoring and other applications described herein.

In contrast to the embodiments described herein, defect review tools are not currently used for inspection purposes because the throughput of defect review tools is substantially lower than inspection tools thereby making inspection using defect review tools highly disadvantageous particularly for in-line monitoring applications. However, as described further herein, discrete locations on wafers are inspected using an electron beam review subsystem to determine if systematic defects are present on the wafers thereby significantly reducing the area on the wafers that is inspected using the electron beam review subsystem and essentially eliminating the throughput concerns of using a defect review tool for inspection purposes.

The computer subsystem may also be configured to identify sources of systematic defects detected on the wafer. The computer subsystem may be configured to identify a systematic defect source using output generated by systematic defect extraction and locations on the wafer that correspond to non-process defects that may produce systematic defects on a wafer. For example, the computer subsystem may be configured to determine if defects detected on the wafer using the images acquired by the electron beam review subsystem are correlated to defects in the design, hot spots, defects on a reticle, defects detected by PWQ analysis, or some combination thereof. In one such example, the computer subsystem may be configured to correlate a defect, which was found using the images acquired by the electron beam review subsystem, to a previously detected and identified systematic defect using combined information from all systematic defect inspections thereby identifying the source of the systematic defect detected on the wafer. The computer subsystem may also be configured to identify a systematic defect source by using a data structure such as a database including all inspection results (e.g., reticle, design, etc.) and a data mining engine that can be used to identify the source of the systematic defect.

In some embodiments, the computer subsystem is configured to use the images acquired at the locations on multiple wafers to monitor the design defects and the process defects at the locations on the multiple wafers. For example, the images may be acquired at the locations on multiple wafers by the electron beam review subsystem, and the computer subsystem may be configured to use the images to detect defects at the locations and to track the defects detected at the same locations over time. In this manner, the embodiments described herein provide methods and discrete defect detection systems for locating and monitoring design defects and systematic or random process defects. In addition, the embodiments described herein integrate within a single system the capability to locate and monitor design defects and systematic or random process defects.

The embodiments also enable semiconductor manufacturing to detect and monitor, within one system, all defect types generated at different phases of chip life, from design to manufacturing. More specifically, the system embodiments provide the unique capability to locate and classify all types of design and process defects within one single system. For example, the system embodiments described herein may be placed at a semiconductor manufacturing fab and used first to scan a design and possibly correct design errors. Then, the system may be used to perform die-to-database inspection to locate defects missed by design scan. In addition, the system may be used to monitor process and/or design hot spots using coordinates found by the design scan and the die-to-database design inspection. Furthermore, the system can be used to review defects found by an optical or SEM wafer inspection system. In this manner, the embodiments described herein may be configured as a single system with the ability to detect and/or locate and monitor both random and systematic defects caused by design and process.

Figure 2:
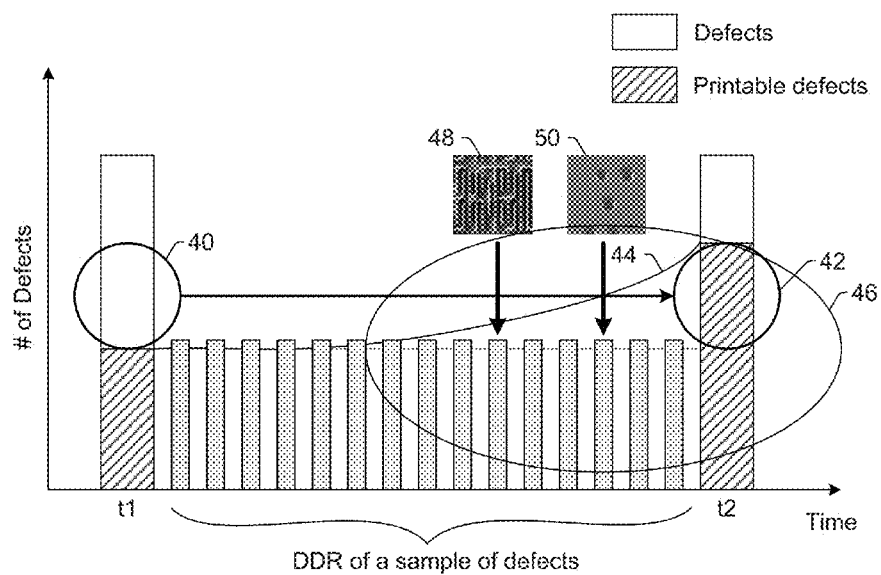
FIGS. 2-3 are schematic diagrams illustrating applications for which the embodiments described herein are particularly useful.

The embodiments described herein may be particularly advantageous for use in applications such as in-line monitoring of reticle defects and contamination. For example, as shown in FIG. 2, at a first point in time (t1), reticle inspection is performed using a system such as the STARlight system. The reticle inspection performed at t1 may be performed for reticle qualification before the reticle is released to manufacturing. As shown in FIG. 2, at t1, a number of defects were detected on the reticle, and the defects include a number of printable defects (i.e., defects that will print on a wafer).

At a second point in time (t2), reticle inspection is again performed using a system such as that described above. The reticle inspection performed at t2 may be performed for reticle re-qualification some period of time after the reticle was released to manufacturing. As shown in FIG. 2, at t1 and t2, approximately the same numbers of total defects were detected on the reticle. However, a greater number of the defects detected at the second point in time are printable defects. Therefore, between t1 and t2, the printability of some of the reticle defects changes. For example, as shown in FIG. 2, circled portion 40 of the number of defects detected at t1 and circled portion 42 of the number of defects detected at t2 illustrate the differences between the numbers of printable defects detected at the two different points in time and the number of defects that may have become printable between the two points in time.

Such a change in the printability of the defects on the reticle may be due to contamination on the reticle that becomes printable defects and are printed, which may cause yield loss. For example, such a change in the printability of the reticle defects may be due to crystal growth defects that initially are not printable but become printable over time. The printability may change after t1 relatively dowdy, but may change much more quickly as t2 approaches, as shown in FIG. 2 by upwardly sloping line 44 between the numbers of defects detected at t1 and t2. If previously non-printable defects become printable defects and are printed on a wafer, these defects may cause yield loss. Therefore, it would be advantageous to detect such defects at the earliest possible time. In particular, it would be advantageous to detect newly printable defects as soon as possible after the number of printable defects begins to increase (e.g., during the time shown by oval 46 in FIG. 2). However, currently available systems and methods may not be able to detect the defects that become printable over time. For example, currently available systems and methods may not be able to detect defects of a size at which the previously non-printable defects become printable.

The embodiments described herein, however, may be used to perform DDR of a sample of defects a number of times at time points between t1 and t2. In particular, DDR may be performed for a sample of locations on the wafer at which the defects detected on the reticle may be printed. For example, DDR may be performed using the reticle inspection results generated at t1 to generate a process in which locations of the non-printable defects detected at t1 in reticle coordinates are inspected on wafers at wafer coordinates corresponding to the reticle coordinates. In addition, the embodiments described herein may be configured for determining wafer coordinates of locations to be reviewed on the wafer based on the reticle inspection results generated at t1, possibly in combination with wafer inspection results acquired at a time point corresponding to the time point at which DDR is being performed. In this manner, the embodiments described herein may be used for determining a sample of defects for which DDR is to be performed based on the reticle inspection results generated at t1 and the wafer inspection results acquired at the time point corresponding to the time point at which DDR is being performed. DDR results may, therefore, be used to determine that at some point in time between t1 and t2, a reticle defect becomes printable. One example of such a defect is shown by image 48 included in FIG. 2. In addition, DDR results may be used to determine that at another later point in time between t1 and t2, another reticle defect becomes printable, one example of which is illustrated by image 50 shown in FIG. 2. Information about the defects that become printable may be used to, for example, determine yield relevancy of the defects that became printable, which may be used to make one or more decisions about the reticle (e.g., repair).

In-line monitoring of reticle defects and contamination described above provides significant value. For example, the embodiments described above may be used to detect printable mask defects as early as possible, which may allow major yield losses to be avoided. In addition, the embodiments described above have substantially high sensitivity to defects due to the substantially high resolution imaging and possibly measurements that may be performed by the system to detect, review, and/or measure the defects. Furthermore, the embodiments described herein provide relatively fast and non-expensive solutions to monitor wafers, which can be performed together with DDR by relatively fast and relatively accurate EBRC.

The embodiments described herein also provide a number of advantages for in-line monitoring of reticle defects and reticle defect classification. For example, the embodiments described herein provide a direct link to reticle inspection systems such as STARlight. In addition, DDR provides substantially high location accuracy. Furthermore, the embodiments described herein provide off-line automatic recipe setup that is capable of dealing with a relatively large number of defects. For example, the embodiments described herein may be configured for automatically detecting a recently completed reticle inspection and automatically creating a monitor plan based on some combination of the design for the wafer as well as the reticle inspection results. This monitor recipe may then be automatically run on some subset of the wafers printed using the inspected reticle.

In some embodiments, the computer subsystem is configured to overlay defect information from multiple process steps in the manufacturing process to identify a design/process interaction issue. The multiple process steps in the manufacturing process may include any of the wafer processing described herein. The defect information that is overlaid may include any of the defect information described herein (e.g., information about defects detected by the computer subsystem using the images acquired by the electron beam review subsystem) possibly combined with defect information acquired at other process steps in a similar or different manner. For example, defect information acquired after a CMP process for the wafer may be acquired in a different manner, but the defect information can still be overlaid with the defect information acquired as described herein. The defect information that is overlaid may include defect information for the entire wafer (e.g., wafers maps can be overlaid). However, the defect information that is overlaid may include defect information for a portion of the wafer (e.g., die stacking). In this manner, defects detected after one process step that may be related to defects detected after another process step can be correlated based on relative positions to thereby provide further information that can be used to determine or identify a design/process interaction issue. In a similar manner, defects detected after one or more process steps that may be related to design defects can be correlated based on relative positions to thereby provide information that can be used to determine or identify a design/process interaction issue.

As described above, the computer subsystem is configured to detect design defects and process defects at the locations on the wafer at which the images are acquired. In this manner, although the system includes an electron beam review subsystem and would therefore be considered a defect review system, the system can perform inspection type functions and produce inspection type results. In addition, the system can perform defect review type functions and produce defect review results 52, as shown in FIG. 1. For example, the embodiments described herein provide methods, defect review tools, and systems that can locate a design or process defect in a defect review process. The defect review type functions may include any suitable defect review type functions. For example, in one embodiment, the electron beam review subsystem is configured to perform CD measurements at the locations. The CD measurements may be performed in any suitable manner.

In another embodiment, computer subsystem 22 is configured to use design clips 38 to classify the design defects and the process defects based on locations of the design defects and the process defects in the design, impact of the design defects and the process defects on a PW for the manufacturing process, impact of the design defects and the process defects on functionality of a device corresponding to the design, or some combination thereof. In this manner, the computer subsystem may be configured to use design clips to classify defects based on locations of the defects in the design and impact of the defects on the PW and/or device functionality.

For example, the computer subsystem may be configured to classify the defects based on design (e.g., design clip-based classification or GDS-based classification). In one such example, after imaging of the locations determined by the computer subsystem, the computer subsystem may perform GDS-based classification for detected defects. GDS-based classification may include aligning an electron beam review subsystem image (e.g., a SEM image) with GDS to remove any "coordinate error" and determine the locations of the defects in the design. The locations of the defects in the design can then be used to determine the design clips corresponding to the locations of the defects. GDS-based classification may use a combination of data extracted from images acquired for the defect location as well as design information, which may be determined from the design clip, at the location of the defect. The design information used for this classification may include additional data such as electrical net lists or film thickness information. The GDS-based classification methodology may include using data extracted from the image acquired for the location of the defect such as whether a defect is a pattern or foreign material type defect, whether the defect is bump or a depression, and whether the defect affects non-dummy patterns on the wafer.

GDS-based classification of defects performed on defect review systems has a number of advantages. For example, such classification can eliminate or reduce the need for manual classification of defects. Eliminating or reducing manual classification can reduce human error during classification. In addition, systematic and random excursions may be detected faster. Furthermore, GDS-based classification can provide "rough CD" and "kill probability" of the detected defects. An additional use of the GDS-based classification is that the defect classification can then drive additional actions at that or other defect locations. One example of such additional actions may be performing material analysis on a defect found to be a fall-on particle. Another example of such additional actions may be to perform additional PW characterization by measuring the same defect location on multiple dies on the wafer if the defect is classified as a pattern defect at a known design hot spot.

In a similar manner, the design clips can be used to determine impact of the defects on the PW of the manufacturing process. For example, the design clips corresponding to the defects can be determined as described above. The design clips can then be used to determine if the defect at the location corresponds to a systematic defect source, which may be performed as described further herein. In this manner, the defects detected on the wafer can be correlated to a systematic defect source, and the effect or impact of the systematic defect source on the PW can be determined from results of PWQ analysis corresponding to the systematic defect source or by performing PWQ analysis for the systematic defect source. The impact on the PW of the systematic defect source correlated to the defect can then be assigned to the defect and used for classification of the defect. For instance, the defect can be assigned a PW-limiting classification or a non-PW-limiting classification.

In addition, the design clips can be used to determine impact of the defects on the device functionality. For example, the design clips corresponding to the defects can be determined as described above. Information about the design corresponding to the locations of the defects can be determined from the design clips, and one or more attributes of the defects can be determined from the images acquired for the locations on the wafer. The information about the design and the one or more attributes may include any of the information and attribute(s) described herein. Such information and attributes may be used as described herein to perform yield simulation to thereby determine the impact of the defects on the device functionality. The impact of the defect on the device functionality can then be used for classification of the defect. For instance, the defect can be assigned a device functionality impacting classification or a non-device functionality impacting classification.

The classification may be performed as described above using the design clips based on some or all of the information described above. For example, classification may be performed based on only the locations of the design defects and the process defects in the design. In another example, classification may be performed based on only the impact of the design defects and the process defects on the PW for the manufacturing process. However, some or all of the information described above may be used in combination to classify the defects. For example, the locations of the design defects and the process defects in the design and the impact of the design defects and the process defects on the functionality of a device corresponding to the design may be used as different attributes of the defects, which in combination are used to classify the defects. Other combinations of the information are also obviously possible.

In another embodiment, the computer subsystem is configured to characterize the design defects and the process defects detected at the locations. For example, the computer subsystem may characterize the located defects using SEM imaging (e.g., relatively high resolution SEM imaging), SEM CD measurements, and other technologies. In addition, the system can be configured to use both disruptive and non-destructive technologies for defect classification. The defect classification may include a defect classification method such as electron beam power assisted classification (ePAC). Examples of methods and systems that can be used to perform ePAC are described in commonly owned U.S. patent application Ser. No. 11/249,144 by Teh et al. filed Oct. 12, 2005 published as U.S. Patent Application Publication No. 2006/0082763 on Apr. 20, 2006, now U.S. Pat. No. 8,532,949 issued on Sep. 10, 2013, which is incorporated by reference as if fully set forth herein. The embodiments described herein may be further configured as described in this patent application. In addition, the system may be configured to perform elemental analysis for defects having sizes greater than about 20 nm. The system may also be configured to perform defect classification as described herein in combination with defect classification of new DOIs located "in-film" and high aspect ratio defects using a delayering method or system such as those described in commonly owned U.S. Pat. No. 7,365,321 to Nasser-Ghodsi et al., which is incorporated by reference as if fully set forth herein. The embodiments described herein may be further configured as described in this patent.

In an additional embodiment, the computer subsystem is configured to compare the images acquired at the locations to design clips to locate the design defects and the process defects at the locations, to classify the design defects and the process defects, to perform relative measurements of the design defects and the process defects, and to perform marginality analysis of the design defects and the process defects. For example, the computer subsystem may be configured to compare SEM images to design clips to locate defects, classify defects, perform relative measurements, and marginality analysis. For instance, the embodiments may use design-based pattern recognition (PR) to locate defects. In particular, the computer subsystem may be configured to identify the locations on the wafer (determined as described herein) during imaging by comparing images acquired by the electron beam review subsystem at the coordinates of the locations to a design for the wafer. In one such example, in order to drive substantially accurately to a location, the computer subsystem may be configured to match some design information with an image of the die acquired by the electron beam review subsystem. The method, called PR, will allow the computer subsystem to substantially accurately identify the locations of the defects.

The system may be configured to locate the defects as described above for automatic defect location (ADL) purposes. For example, one ADL method that may be used by the embodiments described herein is die-to-GDS ADL. This method may include comparing an image of the wafer (e.g., a SEM image, optical microscope (OM) image, or any other type of image) to the design information for the wafer. The image of the die may undergo several image processing operations such as edge map creation and resizing in order to be compared with the design information. The resulting difference image may be used to generate a list of defect candidates and to identify the most probable cause. For instance, multiple differences may be detected or determined in a difference image, and the most probable defect in the difference image may be determined. The coordinates of the most probable defect may then be determined as the defect location.

The computer subsystem may be configured to compare the images to the design clips to classify the design defects and the process defects as described further herein. The computer subsystem may be configured to perform relative measurements of the design defects and the process defects by comparing dimensions of the defects found using the images acquired by the electron beam review subsystem to dimensions of the design. The computer subsystem may be configured to perform marginality analysis based on results of such comparisons. For example, marginality analysis may include determining a kill ratio for defects found using images acquired by the electron beam review subsystem by comparing the found defects to a design for the wafer and/or determining a yield impact for the found defects by comparing dimensions of the found defects to dimensions of the design. In this manner, a defect may be compared to a design for the wafer, and impact on yield may be determined for the defect by comparing defect dimensions to design dimensions.

In a further embodiment, the computer subsystem is configured to perform marginality analysis by performing differential sizing measurements of the design defects and the process defects to determine if the design defects and the process defects are defects or parametric variations, to determine if the design defects and the process defects will impact device performance or reliability, and to determine marginality of the parametric variations versus pre-set marginality threshold values. For example, the computer subsystem may be configured to perform marginality analysis by performing differential sizing measurements of defect and pattern to determine (a) is this a defect or a parametric variation, (b) will this defect impact device performance or reliability, and (c) what is the marginality of the parametric variation versus pre-set threshold values. In one such embodiment, the computer subsystem is configured to perform defect classification based on results of the marginality analysis. For example, defect classification can be based on the above and other criteria. In another such embodiment, the pre-set marginality threshold values are determined using the electron beam review subsystem. For example, marginality threshold values can be determined using a SEM.

In one embodiment, the manufacturing process includes a lithography process, and the computer subsystem is configured to monitor a PW of the lithography process using the images and results of PWQ analysis performed by an inspection tool. For example, the embodiments described herein may also be used for in-line monitoring of design hot spots and PW. In addition, the computer subsystem may be configured to monitor PWs of other manufacturing processes in a similar manner. The inspection tool may include a reticle inspection system or a wafer inspection system such as those described herein and configured to perform PWQ analysis as described further herein. Alternatively, the computer subsystem may monitor the PW using the images and results of PWQ analysis performed by the computer subsystem.

Figure 3:
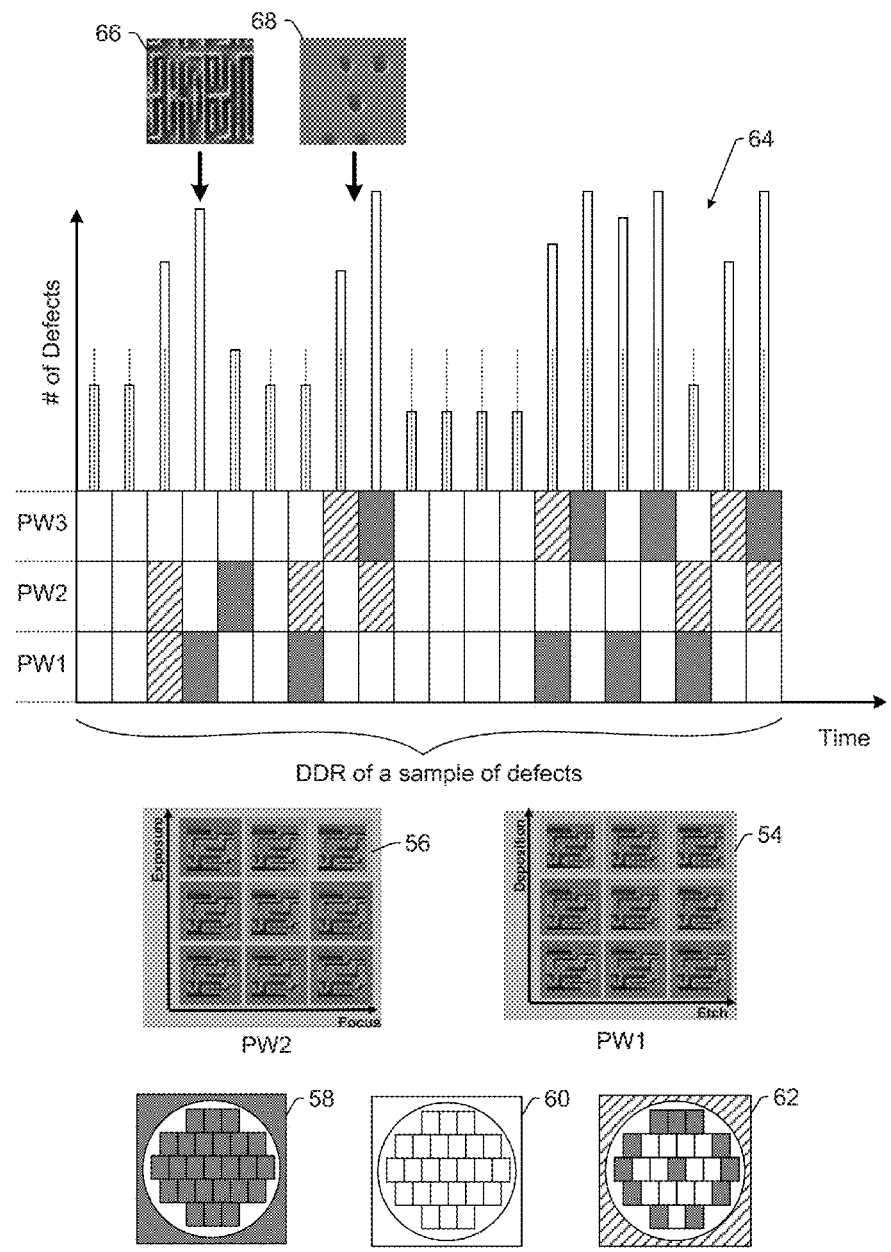

In one such example, as shown in FIG. 3, three different process windows (e.g., PW1, PW2, and PW3) may be monitored over time. The first process window, PW1, is a PW across different values of one or more parameters of a deposition process and different values of one or more parameters of art etch process, as shown by plot 54 in FIG. 3. The one or more parameters of the deposition process and the etch process may include any controllable parameters of these processes. Such a PW may be determined using a number of wafers processed with different sets of values of the one or more parameters of the deposition process and values of the one or more parameters of the etch process. Detecting defects on such wafers may include performing a wafer-to-wafer comparison, which may be performed as described in the above-referenced patent applications by Kulkami et al, and Zafar et al. Wafer-to-wafer comparisons may also be performed in the embodiments described herein as described in commonly owned U.S. patent application Ser. No. 12/234,201 by Bhaskar et al. filed Sep. 19, 2008, which published as U.S. Patent Application Publication No. 2009/0080759 on Mar. 26, 2009, now U.S. Pat. No. 8,126,255 issued on Feb. 28, 2012, and which is incorporated by reference as if fully set forth herein. Such PW inspection may be advantageously performed to detect defects caused by interactions between processes and interactions caused by various values of wafer-level process parameters. The second process window, PW2, is a PW across various values of exposure and various values of dose for a lithography process, as shown by plot 56 in FIG. 3. The third process window, PW3, may be any other suitable PW.

Defects detected by any of the PW inspections may be used to determine if a process has drifted out of the PW, is performing inside of the PW, or is performing near the edge of the PW, as indicated by the wafer maps shown in FIG. 3. In particular, wafer map 58 indicates a process that is out of the PW, wafer map 60 indicates a process that is within the PW, and wafer map 62 showing varying shading of the dies on the wafer indicates a process that is near the edge of the PW. As further shown in FIG. 3 in plot 64, where the processes are operating with respect to the PWs at various points in time affects how many defects are detected on wafers at the various points in time. For example, when a process goes out of its PW as indicated in plot 64 by shading corresponding to wafer map 58, hot spots may turn into defects on the wafer, which may cause yield loss. A process that is within its PW is indicated in plot 64 by shading corresponding to wafer map 60, while a process that is near the edge of its PW is indicated in plot 64 by shading corresponding to wafer map 62.

DDR may, therefore, be advantageously used for in-line monitoring by reviewing a sample of locations on wafers at which systematic defects may have been caused by defects other than process defects at the various points in time, as shown in FIG. 3. For example, DDR can be used to determine that a defect, one example of which is shown in image 66, appears on one or more wafers at the fourth point in time shown in FIG. 3 while a second, different defect, one example of which is shown in image 68, appears on one or more wafers at a later point in time. DDR may be advantageously performed as described above to detect hot spots that turn into defects when a process goes out of its PW, which may cause yield loss.

Such DDR may be performed based on design hot spot information, which may be generated by the computer subsystem, and PW information, which may be generated by PWQ analysis performed by the computer subsystem or another system. For example, the locations determined by the computer subsystem may include locations of design hot spots on the wafer, and the locations of the design hot spots on the wafer may be determined based on output of the design inspection as described further herein. The computer subsystem may use defects detected at the design hot spots to determine if a process is out of the PW. The computer subsystem may also use the defects detected at the design hot spots to determine values of one or more parameters at which the one or more processes were performed on the wafers. For example, the embodiments described herein may include comparing images of the defects acquired by the electron beam review subsystem with images generated by PWQ analysis, and the values of the one or more parameters at which the PWQ analysis was performed corresponding to images that, in at least some respect, match the images acquired by the electron beam review subsystem may be determined as the values of the one or more parameters at which the process was performed on the wafer.

Figure 4:
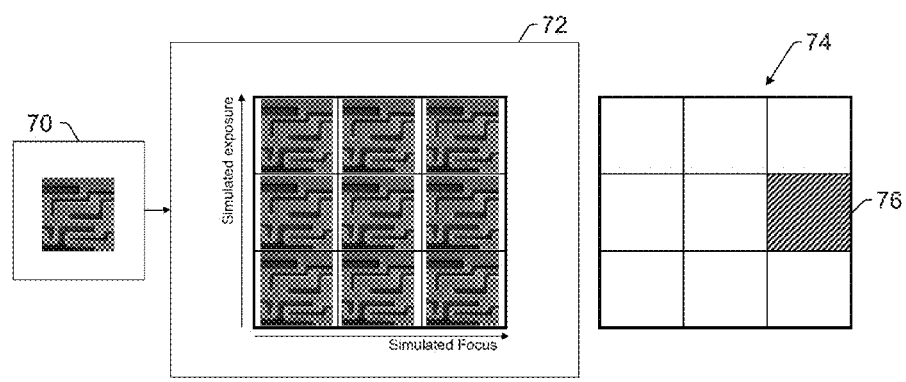
FIG. 4 is a flow chart illustrating one embodiment of a comparison of an image acquired for a discrete location by an electron beam review subsystem and results of process window qualification (PWQ) analysis.

For example, the computer subsystem may be configured to compare, as shown in FIG. 4, image 70 of a die (a wafer image) acquired by the electron beam review subsystem at coordinates of a location determined as described herein to a simulated (or rendered) PW matrix of images 72 of the die under different process conditions. The simulated matrix may be created by predicting the resulting image of the die for a given design when two or more parameters of the PW (e.g., focus and exposure) vary. In addition, the current sample image may be compared to a plurality of sample images representing various points in the PW, and the plurality of sample images may be stored in a data structure such as a library. Therefore, the embodiments may be configured for matching (or attempting to match) the current sample image against a library of stored sample images representing various points in the PW.

In one such embodiment, the computer subsystem may be configured to monitor the PW of the lithography process by determining information about the process based on results of the comparing step described above. For example, as described above, the computer subsystem may compare the image of the die to the simulated matrix to determine if the image matches one of the matrix components. Therefore, such comparing may provide the user with some information about the process used to produce the die. For example, as shown in FIG. 4, one of the simulated PW matrix images may be determined to match the wafer image, and the simulated PW matrix image that is determined to match the wafer image is indicated in results 74 in which the position of the simulated PW matrix image that matched the wafer image within the PW matrix is indicated by shading 76 shown in FIG. 4. Therefore, the comparison described above may be used to determine the focus and/or exposure values that caused the defect. In this manner, when PWQ analysis is performed, the effect of focus and exposure on the printing of the design can be determined. How the defect appears in the image of the wafer may then be used to determine how much the values of the parameters are off from the PW center. In this manner, the embodiments described herein can be used to detect and monitor drifts in one or more parameters of a process tool. Such information can be fed back to the process system or any other system that can be used to alter and/or correct the values of the parameters of the process used to fabricate the wafer on which the defect was detected, which may be performed as described further herein.

In a similar manner, the computer subsystem may be configured to identify the locations on the wafer during imaging by comparing images acquired by the electron beam review subsystem at the coordinates of the locations to simulated images that illustrate how the design would be printed on the wafer at different values of one or more parameters of a process performed on the wafer. In this manner, another ADL method that may be performed by the computer subsystem is die-to-process window matrix ADL.

In-line monitoring performed as described above using DDR, design hot spot information, and results of PWQ analysis provides significant value for semiconductor manufacturing. For example, DDR allows detection of defects on wafers caused by design and/or photo defects as early as possible, which may allow major yield losses to be avoided. In addition, using DDR for in-line monitoring as described above provides substantially high sensitivity for defects due to the substantially high resolution imaging and possibly measurements that can be used for DDR. Furthermore, results of design inspection may be used to determine if a defect was not detected by an optical inspection system or an electron beam inspection system. In particular, DDR may be used to detect defects that could not be detected by optical or electron beam inspection. Such DDR may be performed using, for example, relatively high resolution SEM imaging, relatively high resolution tilt SEM imaging, focused ion beam (FIB) imaging, or some combination thereof. Furthermore, using DDR for in-line monitoring as described above provides a relatively fast and non-expensive solution for monitoring wafers, which can be performed together with relatively fast and relatively accurate EBRC.

In-line monitoring performed as described above using DDR also provides a number of advantages over other methods and systems for in-line monitoring. For example, the embodiments described herein provide a direct link to design inspection results and PWQ inspection results. In addition, DDR provides substantially high location accuracy. Furthermore, the embodiments described herein provide off-line automatic recipe setup that allows relatively large numbers of defects to be dealt with effectively. For example, the embodiments described herein may be configured for automatically detecting a recently completed PWQ analysis and automatically creating a monitor plan based on some combination of the design for the wafer as well as the results of the PWQ analysis. This monitor recipe may then be automatically run on some subset of the wafers on which the process is performed (wafers processed using the process for which PWQ analysis was performed).

Each of the embodiments of the system described above may be further configured as described herein. In addition, the embodiments of the system described above may be configured to perform any step(s) of any method embodiment(s) described herein.

Another embodiment relates to a system configured to review defects on a wafer. This system includes an electron beam review subsystem configured to acquire images for discrete locations on a wafer on which a design is printed using a manufacturing process. For example, the system may include electron beam review subsystem 10 as shown in FIG. 1. The design may be printed on the wafer using any of the manufacturing processes described herein.

The system also includes a computer subsystem configured to determine the discrete locations based on results of PWQ analysis. For example, the system may include computer subsystem 22 shown in FIG. 1 configured to determine locations 30 (discrete locations) for which images on wafer 12 will be acquired by electron beam review subsystem 10 based on results of the PWQ analysis. The computer subsystem may be configured to determine the discrete locations based on the results of the PWQ analysis as described further herein. For instance, the computer subsystem may determine the discrete locations for which the images on the wafer will be acquired by translating coordinates of defects detected by PWQ analysis into coordinates on the wafer.

The results of the PWQ analysis may be generated using any PWQ analysis method described herein. In one embodiment, the PWQ analysis is performed by an inspection system. For example, an inspection system (e.g., a wafer inspection system, which may include any of the wafer inspection systems described herein) may be configured to perform PWQ analysis by generating images of a reticle printed on one or more wafers at different values of process parameters and comparing the images to detect defects on the reticle. In one embodiment, the computer subsystem is configured to import the results of PWQ analysis from a system that performed the PWQ analysis. For example, the computer subsystem may be configured to import PWQ analysis results into the review SEM for discrete inspection site selection and recipe setup. In this manner, the computer subsystem may have connectivity to a PWQ analysis system, which is advantageous as described further herein.

The results of PWQ analysis may include any information that is or can be generated by PWQ analysis, and the PWQ analysis results may have any suitable format. In one embodiment, the results of the PWQ analysis include defect locations, classification information related to the analysis, and images acquired for the analysis. For example, results of a typical PWQ analysis is in the form of a KLARF or Lot Result file containing defect locations, classification information as related to the analysis, and images (e.g., optical patch images). In this manner, the computer subsystem may acquire all of the results of PWQ analysis and can use some or all of the PWQ results as described further herein.

In one embodiment, the results of the PWQ analysis include classification information, and the computer subsystem is configured to use a file containing the results of the PWQ analysis to create a recipe for monitoring the discrete locations on multiple wafers. For example, PWQ analysis can identify sites that are on the edge of the PW and are likely to fail if the process deviates from the nominal and hence should be monitored regularly. In addition, PWQ analysis provides defect classification information identifying defects of varying probability of failure. The system may use the file containing the results of the PWQ analysis and classification information to monitor these sites. In this manner, the review SEM may use the PWQ analysis results to create a recipe specifying the locations to visit and inspect for a defect.

The computer subsystem may be configured to create a recipe for defect review and/or monitoring the discrete locations using coordinates of the locations determined as described herein and a design for the wafer. Setup may be preformed "off-line" without the need for imaging of the wafer and/or defects on the wafer. In this manner, the computer subsystem may be configured to create a systematic defect review recipe. For example, the capability to drive relatively accurately to a defect location is particularly advantageous for systematic defect review. The computer subsystem may be configured as, be configured to use, or include a design-based setup engine that uses some design information (e.g., information about the design to be printed on the wafer and the layout in which the design will be printed on the wafer) to automatically setup a recipe that will allow the review system to locate the systematic defects. In addition, systematic defect review sample and recipe creation may be performed as described further herein using output generated by design inspection, reticle inspection, and PWQ analysis.

In another embodiment, the computer subsystem is configured to determine the discrete locations based on the results of the PWQ analysis and results of inspection of a reticle by reticle inspection system 34, which may be performed as described further herein. In some embodiments, the computer subsystem is configured to determine the discrete locations based on the results of the PWQ analysis, defects in the design detected by inspection of the design, additional defects in the design detected by comparing an image of a die in the design printed on the wafer to an image of the die stored in a database, and defects detected on the wafer by a wafer inspection system, which may be performed as described further herein.

In one embodiment, the electron beam review subsystem includes an optical microscope (OM). For example, as shown in FIG. 1, electron beam review subsystem 10 may include OM 78. The OM may have any suitable configuration. For example, the OM may include lens 80 configured to focus light to wafer 12 and to focus light reflected from the wafer to detector 82. In addition, the OM may include a number of other components that are not shown in FIG. 1 such as a light source, one or more apertures, one or more filters, one or more polarizing components, and the like. Such components and suitable arrangements of the components within the OM are generally known in the art and therefore will not be described further herein for the sake of brevity. The detector of the OM is configured to generate images 84 for discrete locations on wafer 12. The images generated by the OM may have any suitable format and may include any suitable images (e.g., optical patch images). The images generated by the detector of the OM may be provided to computer subsystem 22 such that the computer subsystem can perform one or more functions described herein using the images. The detector and the computer subsystem may be coupled as described further herein such that the computer subsystem can receive the images generated by the detector of the OM.

As shown in FIG. 1, OM 78 may be spaced from electron column 14 within the electron beam review subsystem. In some such configurations, stage 18 may be configured to move the wafer between the electron column and the OM depending on which images are being acquired for the wafer. For example, stage 18 may be configured to move wafer 12 from a position under electron column 14 in a direction shown by arrow 20 such that the wafer is positioned under the OM as shown in phantom in FIG. 1. However, the OM and the electron column may have any suitable configuration within the electron beam review subsystem.

In one such embodiment, the computer subsystem is configured to identify the discrete locations on the wafer using images for the discrete locations acquired by OM 78 and optical patch images for the discrete locations acquired by wafer inspection system 32. For example, the review sites can be relocated and visited using an OM ADL approach in which the optical patch images from the inspection system and the OM onboard the SEM can be used to accurately pinpoint the location to be inspected. In one such example, an image acquired by OM 78 at one of the discrete locations can be compared to an optical patch image for the same location acquired by the wafer inspection system. If the images do not substantially match, the field of view (FOV) of the OM on the wafer may be altered and another image can be acquired by the OM and compared to the optical patch image until the optical patch image substantially matches the image acquired by the OM. Other functions may be performed on the OM image and the optical patch image prior to comparison (e.g., to account for differences between the optics of the OM and the wafer inspection system).

In some such embodiments, the system is configured to position the discrete locations in a FONT of the electron beam review subsystem based on the identified discrete locations. For example, information about the discrete location identified using the OM can be used to position the same location on the wafer in the FOV of the electron column with substantially high accuracy (e.g., depending on the spatial relationship between the OM and the electron column). In this manner, the system, which may be configured as a review SEM, can use an OM ADL approach to substantially accurately position the desired site within the SEM FOV. Positioning the locations in the FOV of the SEM in this manner allows the SEM to use a smaller (e.g., less than 2 μm) FOV to capture site images and eliminates the need for grabbing a reference image thereby saving move-acquire-measure (MAM) time and increasing throughput. In addition, using the OM ADL approach significantly reduces the chance of imaging the wrong location as defects get smaller with each technology node. The OM ADL approach also eliminates the need for setting up PR for each site, which would be necessary for other tools that do not have access to optical patch images in PWQ Lot results. In this manner, using the OM ADL approach allows for faster and simpler recipe setup as well as faster defect review.

In one embodiment, the computer subsystem is configured to determine if defects exist at the discrete locations using the images acquired for the discrete locations by the electron beam review subsystem. For example, the review SEM may visit the locations specified in a recipe and use software algorithms to determine if there is a defect at that location. The computer subsystem may be configured to use any defect detection methods, algorithms, and techniques to determine if defects exist at the discrete locations including those described further herein.

The computer subsystem included in this system embodiment is also configured to perform defect review at the discrete locations using the images acquired for the discrete locations by the electron beam review subsystem. In this manner, the system may be configured to review discrete locations on semiconductor wafers using a review SEM tool (e.g., a SEM review tool commercially available from KLA-Tencor) with the locations being identified through PWQ analysis. In contrast, users of defect review systems currently use prior knowledge of process parameters and defectivity to identify the locations on wafers to review. However, identifying the locations on the wafers to review in this manner has a number of disadvantages. For example, the method does not involve a process-based and/or design-based analysis. Instead, the method relies on the user's prior knowledge and therefore may not cover all possible defect sites. In addition, the method may not be consistent from one user to another and from one process step or layer to another. The method is also manual and time consuming to set up. Furthermore, the method requires the user to set up PR locations for each site to ensure the correct features are centered within the FOV of the electron beam review subsystem. In contrast, the embodiments described herein are configured to select review sites intelligently and automatically based on PWQ analysis without relying on user knowledge. Selecting the review sites in this manner provides consistency across multiple process steps/layers/devices/users/etc. In addition, using the embodiments described herein, all potential weak spots in the process can be captured and reviewed thereby reducing the chance of missing any failure sites.

The computer subsystem may be configured to perform defect review at the discrete locations in a number of different ways. For example, the computer subsystem may be configured to perform defect classification based on the marginality of the defect (e.g., the severity of its impact on the functionality of the semiconductor device). Such classification may be performed using DBB, which may be performed as described further herein. The computer subsystem may also be configured to perform defect review at the discrete locations according to any of the embodiment(s) described herein.

In one embodiment, the results of the PWQ analysis include Bossung images, and the computer subsystem is configured to perform the defect review at the discrete locations by comparing the Bossung images to the images acquired for the discrete locations by the electron beam review subsystem. For example, a series of Bossung images can be stored and compared against, which would not be possible without linkage to PWQ analysis results. The Bossung images may include images such as those shown in FIG. 4 and the comparison of the images acquired for the discrete locations to the Bossung images may be performed as described further herein.

In another embodiment, the computer subsystem is configured to extract images corresponding to the design printed at nominal values of one or more parameters of the manufacturing process from the results of the PWQ analysis and to use the extracted images to create a recipe for monitoring the discrete locations on multiple wafers. For example, linking to PWQ analysis provides the added benefit of extracting "golden" or reference images corresponding to nominal conditions to compare against thereby speeding up and simplifying the recipe setup process.

Each of the embodiments of the system described above may be further configured as described herein. In addition, each of the embodiments of the system described above may be configured to perform any step(s) of any method embodiment(s) described herein.

An additional embodiment relates to another system configured to review defects on a wafer. This system includes an electron beam review subsystem configured to acquire images for discrete locations on a wafer on which a design is printed using a lithography process performed with a reticle. For example, the system may include electron beam review subsystem 10 as shown in FIG. 1. The system also includes a computer subsystem configured to determine the discrete locations based on results of inspection of the reticle. For example, the system may include computer subsystem 22 shown in FIG. 1 configured to determine locations 30 (i.e., discrete locations) based on results of inspection of the reticle. The computer subsystem may be configured to determine the discrete locations based on the results of the inspection of the reticle according to any of the embodiments described herein.

In one embodiment, the computer subsystem is configured to acquire a file from a reticle inspection system. For example, computer subsystem 22 may acquire a file from reticle inspection system 34. The computer subsystem may be coupled to the reticle inspection system as described further herein such that the computer subsystem can acquire the file from the reticle inspection system. The file includes the results of the inspection of the reticle, design coordinates, and design clips. In one such embodiment, the computer subsystem is configured to use the results of the inspection, the design coordinates, and the design clips to translate reticle coordinates into wafer coordinates. For example, the system (SEM) could connect with the reticle inspection system by importing their inspection results files that may include design coordinates and design clips to translate the reticle coordinates onto the wafer. The computer subsystem may use the inspection results, the design coordinates, and the design clips as described further herein to translate the reticle coordinates into wafer coordinates.

The computer subsystem may also be configured to determine the discrete locations based on any other information described herein (e.g., results of inspection of the reticle, defects in the design detected by inspection of the design, additional defects in the design detected by comparing an image of a die in the design printed on the wafer to an image of the die stored in a database, defects detected on the wafer by a wafer inspection system, and results of PWQ analysis performed for the reticle).

The computer subsystem is also configured to perform defect review at the discrete locations using the images acquired for the discrete locations by the electron beam review subsystem, the results of the inspection of the reticle, and classification of defects detected on the reticle. In one embodiment, the classification of the defects detected on the reticle is performed by a reticle inspection system. In this manner, the computer subsystem may be configured to review discrete locations on semiconductor wafers using the results of reticle inspection and defect classification by reticle inspection tools such as STARlight, Starlight-2, and TeraScan reticle inspection systems that are commercially available from KLA-Tencor. As such, the computer subsystem can use the SEM review tool to cross-check the defects identified and classified by STARlight and other reticle inspection systems. The computer subsystem may also be configured to perform such defect review as described further herein.

In some embodiments, the computer subsystem is configured to position the discrete locations in a FOV of the electron beam review subsystem based on design clips corresponding to the defects. In this manner, design clips can be used to place the discrete locations in the FOV of the SEM. As such, the computer subsystem may be configured to perform ADL by comparing the images acquired by the electron beam review subsystem to design clips. The computer subsystem may be configured to position the discrete locations in the FOV of the electron beam review subsystem based on the design clips as described further herein. Another example of an ADL method that may be performed by the computer subsystem is die-to-reticle inspection optical patch image ADL. The patch images may include OM images. This method may include comparing a relatively high resolution optical image of the die with a relatively high resolution optical image previously generated by the reticle inspection system. The comparison enables re-location of the defect with substantially high accuracy.

In one embodiment, the discrete locations include discrete locations of the defects that affect a PW of the lithography process, discrete locations of the defects that do not affect the PW, discrete locations of the defects that print on the wafer, and discrete locations of the defects that do not print on the wafer such that all marginal defects on the reticle are reviewed and captured. In this manner, the SEM can be used to review and capture all marginal "on edge" defects.

In one embodiment, the discrete locations include discrete locations of defects having a size that renders them undetectable by a bright field (BF) optical wafer inspection system, and the computer subsystem is configured to perform differential sizing analysis of the defects that cannot be detected by the BF optical wafer inspection system. In this manner, the SEM can perform differential sizing analysis on substantially small defects that are typically missed by BF inspection systems. In some embodiments, the computer subsystem is configured to perform differential sizing analysis of defects at the discrete locations by comparing feature dimensions in the images acquired for the discrete locations to dimensions of neighboring features in the same die as the discrete locations. For example, differential sizing analysis can be performed by comparing feature dimensions to neighboring features rather than to neighboring dies. Absolute measurements are not necessary for this analysis. The embodiments described herein, therefore, may advantageously provide additional features on a SEM review system including differential sizing.

In one embodiment, the computer subsystem is configured to compare the images acquired for the discrete locations with design clips corresponding to the defects to compare the images to design intent (e.g., how the designer intended the design to be printed on the wafer). For example, the design clips can be used not only to place the defect in the FOV of the electron beam review subsystem, which may be performed as described above, but also to compare the SEM image with design intent. Results of comparing the images acquired for the discrete locations to the design intent can be used to classify the defects on the reticle based on how they printed on the wafer and how they printed differs from the design intent. Such comparison of the images to the design clips and classification of the defects based on results of such comparison may be performed as described further herein. In this manner, the embodiments described herein may advantageously provide additional features on a SEM review system including enhanced reticle inspection system e.g., STARlight) defect classification.

In another embodiment, the computer subsystem is configured to compare the images acquired for the discrete locations to images of a die stored in a database. Comparing the images acquired for the discrete locations to images of the die stored in the database may be performed as described further herein. In this manner, the embodiments described herein may advantageously provide additional features on a SEM review system including die-to-database capability.

In one embodiment, the computer subsystem is configured to monitor variations in a PW of the lithography process caused by the defects detected on the reticle using the results of the inspection of the reticle and the images acquired for the discrete locations by the electron beam review subsystem. The computer subsystem may be configured to monitor the variations in the PW in this manner according to any of the embodiments described further herein. In this manner, the computer subsystem can be used to perform a method for monitoring lithography PW variations caused by reticle defects using a SEM review tool and reticle inspection results.

The embodiments described herein provide a number of advantages over other methods for monitoring variations in the lithography PW. For example, currently, IC manufacturers inspect reticles at various stages, including: when the reticles arrive new from the mask shops; during production at a certain frequency based on number of wafers processed or time elapsed; and after repair of the reticles and before putting the reticles back in production. Defects on the reticle are optically reviewed and classified. Customers rely on this information to make decisions about whether a reticle is acceptable for production, needs repair, or should be discarded. Some IC manufacturers want to correlate the reticle inspection results to actual results on the wafer. One method to do that is to use an "Image Qual" technique to look for the start of repeater defects, in that method, the reticle is printed on resist-on-silicon wafers and BF inspection is used to pick up the repeater defects.

However, reticle inspection systems such as STARlight reticle inspection systems have substantially high sensitivity and detect a substantial number of defects that may not affect the PW or may not even print on the wafer. There is no effective way to check the wafers to see if the marginal defects are printing. While the Image Qual method can be used to detect defects on the wafer, by the time BE tools identify the defects it may be too late for the reticle. In other words, the process may have to be stopped cold. This method is also limited by the sensitivity of BF inspection systems and their ability to identify repeater defects originating from the reticles. Another drawback of the Image Qual method is the requirement to inspect the entire die and filter out the nuisance random defects from true repeater defects. Hence, neither of these methods provides a practical way to flag reticle defects before they start impacting the lithography PW.

In contrast, the embodiments described herein can be used to flag reticle defects before they start impacting the lithography PW and can be used to address issues with the current Image Qual techniques. In addition, the embodiments described herein incorporate the benefits of existing methods while enhancing the overall performance of those existing methods. Furthermore, the embodiments described herein may advantageously provide additional features on a SEM review system that can be used to extend the life of reticles (e.g., reticles designed for 193 nm wavelength lithography).

In one embodiment, the computer subsystem is configured to append the images acquired for the discrete locations to a file that includes the results of the inspection of the reticle, and a reticle inspection system is configured to use the images appended to the file to setup a recipe for reticle inspection. For example, after SEM review, the SEM images can be appended back to the inspection results file to be used by other reticle inspection systems for better recipe setup. The computer subsystem may append the images to the reticle inspection results file in any suitable manner. Appending the images acquired for the discrete locations by the electron beam review subsystem to the file advantageously allows a reticle inspection system to compare the images acquired by the electron beam review subsystem to the results of the inspection for the same locations. In this manner, the reticle inspection system can use the images appended to the file to determine more information about the defects that were detected by the reticle inspection system such as whether the defects detected by reticle inspection are actual defects, are actual defects that print, or are actual defects that do not print in a manner that affects the PW, device characteristics, etc. In addition, based on the additional information about the defects determined by the reticle inspection system, the reticle inspection system can determine one or more parameters of an inspection recipe such that fewer defects that are not actual defects, are actual defects that do not print, or do not affect printing in a manner that reduces the PW, device functionality, etc. are detected by inspection while more defects that are actual defects, actual defects that print, and do affect the printing in a manner that reduces the PW, device functionality, etc. are detected by the inspection. The one or more parameters of the inspection recipe that may be determined and/or altered by the reticle inspection system based on the file containing the appended images may include any adjustable parameters of the reticle inspection tool including output acquisition parameters (e.g., optical parameters such as angle of incidence, polarization and/or wavelength of illumination, collection angle, polarization of detection, and the like) and defect detection parameters (e.g., defect detection threshold, defect detection method or algorithm, one or more parameters of filtering, and the like). In addition, such alteration and/or setup of reticle inspection recipes may be performed by the computer subsystem using the file that includes the results of the inspection of the reticle and the images acquired at the discrete locations as described above.

In another embodiment, the computer subsystem is configured to append the images acquired for the discrete locations to a file that includes the results of the inspection of the reticle, and a computer-implemented method includes using the images appended to the file to setup a recipe for inspection of an additional design. For example, after SEM review, the SEM images can be appended back to the inspection results file to be used by DesignScan simulation software for better recipe setup. The computer subsystem may be configured to append the images to the file in any suitable manner. Appending the images acquired for the discrete locations by the electron beam review subsystem to the file advantageously allows a computer-implemented method to compare the images acquired by the electron beam review subsystem, the results of the inspection, and defects that were detected by the design inspection at corresponding locations. In this manner, the computer-implemented method can use the images appended to the file and the reticle inspection results to determine more information about the defects that were detected by the design inspection such as (1) whether the defects detected by design inspection produced defects on the reticle and (2) if the design defects produced defects on the reticle, if the defects on the reticle produced actual defects on the wafer, produced actual defects on the wafer that do not print in a manner that affects the PW, device characteristics, etc. In addition, based on the additional information about the defects determined by the computer-implemented method, the computer-implemented method can determine one or more parameters of a design inspection recipe such that fewer defects that do not produce defects on the reticle, produce defects on the reticle that do not produce actual defects on the wafer or do not affect printing on the wafer in a manner that reduces the PW, device functionality, etc. are detected by design inspection while more defects that produce defects on the reticle, produce defects on the reticle that produce actual defects on the wafer and do affect the printing in a manner that reduces the PW, device functionality, etc. are detected by design inspection. The one or more parameters of the design inspection recipe that may be determined and/or altered by the computer-implemented method based on the file containing the appended images may include any adjustable parameters of the design inspection recipe. In addition, the computer subsystem may be configured to perform the computer-implemented method for setting up a recipe for inspection of an additional design using the images appended to the file as described above.

In an additional embodiment, the computer subsystem is configured to alter a recipe for inspection of reticles based on results of the defect review at the discrete locations. For example, the SEM could include the capability of figuring out settings on the reticle inspection system to minimize the number of nuisance defects detected based on the SEM review results. In this manner, the embodiments described herein may be used for review inspection cycle optimization (RICO) by using results generated by the review system to alter and even optimize inspection recipes (e.g., like RICO for reticle inspection systems). The computer subsystem may be configured to alter the recipe for inspection of reticles based on the results of the defect review at the discrete locations as described further herein.

The computer subsystem may also be configured to alter one or more parameters of one or more inspection systems based on results of the defect review. The one or more inspection systems may include any inspection system, defects detected by which were used by the computer subsystem to determine locations on the wafer at which images are acquired by the electron beam review subsystem. For example, the computer subsystem may be configured to generate system feedback to inspection, design, reticle, photo (lithography), or some combination thereof. The computer subsystem may also be configured to optimize a systematic defect inspection system using a systematic defect review system. For example, the computer subsystem may be configured to calibrate an inspection system (e.g., design inspection system, reticle inspection system, etc.). In such embodiments, results of DDR may be made available to the original systematic defect inspection system. For each of the defects, the embodiments may use and/or provide the user with the inspection system parameters and the review results to enable fine tuning and/or calibration of the inspection systems.

In a further embodiment, the computer subsystem is coupled to a reticle inspection system such that the computer subsystem can send information to the reticle inspection system and receive information from the reticle inspection system. In this manner, the embodiments described herein may advantageously provide additional features on a SEM review system including connectivity to reticle inspection systems (e.g., STARlight inspectors). The computer subsystem may be coupled to the reticle inspection system as described further herein. In addition, the computer subsystem may send any of the information described herein to the reticle inspection system, and the information received by the computer subsystem from the reticle inspection system may include any information generated by the reticle inspection system. The reticle inspection system may perform one or more functions described herein using the information received from the computer subsystem, and the computer subsystem may perform one or more functions described herein using the information received from the reticle inspection system.

Each of the embodiments of the system described above may be further configured according to any other system embodiments described herein. In addition, each of the system embodiments described above may be configured to perform any step(s) of any method embodiment(s) described herein.

Each of the embodiments described above may also be further configured or be configured to perform any step(s) of any method(s) described in commonly owned U.S. patent application Ser. No. 11/950,961 to Fouquet et al. filed Dec. 5, 2007, which published as U.S. Patent Application Publication No. 2008/0163140 on Jul. 3, 2008, now U.S. Pat. No. 7,904,845 issued on Mar. 8, 2011, and which is incorporated by reference as if fully set forth herein.

A further embodiment relates to a computer-implemented method for selecting one or more features within a design for use as process monitoring features % In particular, as will be described further herein, the computer-implemented method can be used to select "smart canaries" for semiconductor process control. The method includes simulating how features in a design will print on a wafer at different values of one or more parameters of a lithography process, as shown in step 92 of FIG. 6. The different values include nominal values corresponding to a center of a PW of the lithography process. The simulating step can be performed using a PW microlithography simulation tool such as DesignScan, which is commercially available from KLA-Tencor. For example, the simulating tool simulates the lithography process including process parameter variations. In addition, the simulating step may include simulating the printing of the design using a lithography simulation tool such as DesignScan that is calibrated to the process that is being used to print the wafers. Furthermore, the definition of PW can extend well beyond just focus and exposure of the lithography process. For example, the embodiments described herein can be extended to cover any process parameter or combination of parameters of the microlithographic process. In addition, the different values of the one or more parameters of the lithography process for which the simulating step is performed may span an entire predetermined PW for the lithography process and may even extend beyond the entire predetermined PW. The different values of the one or more parameters of the lithography process for which the simulating step is performed may also have any suitable increments (e.g., granularity) across the range of different values for which the simulating step is performed.

The simulating step may also be performed as described in commonly owned U.S. patent application Ser. No. 11/048,630 by Saidin et al. filed Jan. 31, 2005, which published as U.S. Patent Application Publication No. 2006/0236294 on Oct. 19, 2006, now U.S. Pat. No. 7,646,906 issued on Jan. 12, 2010, which is incorporated by reference as if fully set forth herein. The embodiments described herein may include any step(s) of any method(s) described in this patent application. Examples of methods and systems that can be used to create a wafer fabrication process are described in commonly owned U.S. patent application Ser. No. 11/374,710 by Hess filed Mar. 14, 2006, which published as U.S. Patent Application Publication No. 2006/0161452 on Jul. 20, 2006, now abandoned, and which is incorporated by reference as if fully set forth herein. The embodiments described herein may include any step(s) of any method(s) described in this patent application.

Figure 6:
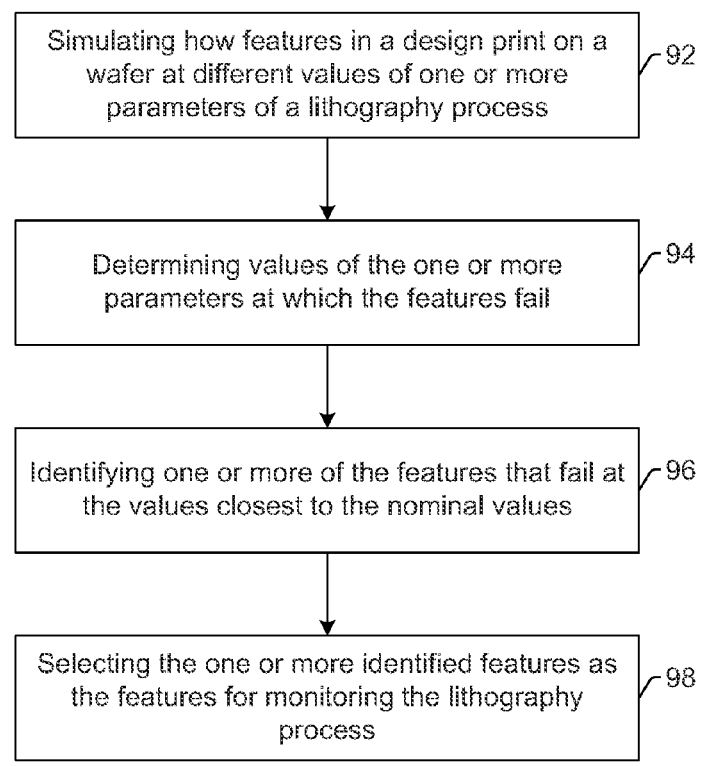
FIG. 6 is a flow chart illustrating one embodiment of a computer-implemented method for selecting one or more features within a design as processing monitoring features.

The method also includes determining values of the one or more parameters at which the features will fail, as shown in step 94 of FIG. 6. For example, determining the values of the one or more parameters at which the features will fail may include comparing results of the simulating step (e.g., simulated images) to criteria defining acceptable characteristics of the features. In one such example, determining the values at which the features will fail may include determining one or more characteristics of the features such as CD and comparing the determined CDs to acceptable CDs of the features which may be defined by the design. However, determining the values at which the features will fail may include detecting defects in the features that will be printed on the wafer by comparing the simulation results (e.g., simulated images) to a reference for the features (e.g., a simulated image illustrating how the features will be printed at the nominal values or a design clip corresponding to the features). The defects detected in the features may be analyzed to determine if the defects will affect the device being fabricated on the wafer. If the defect affects the device to such an extent that it reduces parametric characteristics of the device, prevents functioning of the device, reduces yield of the manufacturing process, or some combination thereof, the features containing that defect may be determined to have failed.

The results of the simulating step for each of the different values may be used as described above to determine if the features fail at each of the different values. However, the results of the simulating step for features at a subset of the different values (i.e., only a portion of the different values) may be used as described above to determine the values at which the features will fail. For example, determining the values of the one or more parameters at which the features will fail may begin using the results of the simulating step corresponding to the nominal values and then proceed moving away from the nominal values until the results of the simulating step indicate that the features have failed. For example, once a feature fails at one value of the one or more parameters of the lithography process, that feature will generally also fail or fail more drastically as the values move farther away from nominal. Therefore, based on the first value from nominal at which the features are determined to have failed, the features can also be determined to have failed at values farther from nominal than the first value without actually analyzing the simulating results for those values farther from nominal.

In addition, the method includes identifying one or more of the features that will fail at the values closest to the nominal values, as shown in step 96 of FIG. 6. For example, the identifying step may include identifying the features in the design that are most prone to failure while varying the process parameters of interest (e.g., focus and exposure) from their nominal values. In this manner, results produced by simulation (which may be performed using a lithography simulation tool such as DesignScan) can be used to identify features within a design and subsequently on a wafer that are weaker and potentially prone to fail most readily. For example, certain geometries within a design will start to fail at process parameter values (e.g., focus and exposure) that are closer to the nominal values than the remainder of the regions of the design. In this manner, the results of the simulating step can be used to identify which figures among all figures in a design will fail closest to the center of the PW. The one or more features that will fail at the values closest to the nominal values may be identified using the results of the determining step described above (e.g., the values closest to nominal values at which different features will fail may be compared to identify which of the different features will fail at values closest to nominal).

The method further includes selecting the one or more identified features as the features to be used for monitoring the lithography process, as shown in step 98 of FIG. 6. Those features can then become "canary" features in that they provide an early indication of a process problem. In this manner, the method may use full chip, PW lithographic simulation results to automatically select the canary features. The one or more identified features and possibly other features may be selected for monitoring the lithography process as described further herein.

In one embodiment, using the one or more selected features for monitoring the lithography process allows deviations in the lithography process to be detected by the monitoring before the deviations become yield limiting. For example, the embodiments described herein provide for better microlithographic process control so that a deviation in the semiconductor manufacturing process can be detected, analyzed, and corrected before the process deviation becomes yield limiting for the semiconductor device being manufactured. Such process control is accomplished with "canary" features that act as the early indicators of a problem with the process. By utilizing detailed information from these features, an earlier indication of a process problem and an analysis of the specifics of the problem can be achieved. In the process control arena, the ability to have the earliest indicator of a process problem can prevent yield limiting defects from stopping a wafer production line.

In contrast, currently, there are specific process monitoring features that are placed in the inactive areas of a reticle design. These monitoring features are printed on the wafer during the microlithography process and are subsequently measured and monitored with a CD SEM or other appropriate metrology tool. Excess deviations in the CD of a monitored feature are an indication of a problem or deviation in the process being used to manufacture the wafer.

Such process monitoring features, however, have a number of disadvantages. For example, the process monitoring features used in the current methodology are limited in their scope. As such, they typically do not represent the weakest portion of the device design and will not give as early an indication of a process deviation or how near the device is to failure. This delay in the determination of the process deviation will potentially allow the process deviation to become yield-limiting before the process can be corrected. In addition, there is insufficient information from these features to be able to properly analyze specifically what process deviation took place. There may be some indication of a problem with the process, but more time, data, and analysis would be required to determine the specific type of deviation so that corrective action can be taken.

A broad range of canary features can be chosen. The chosen features can be prioritized not only based on their propensity for early failure, but also for the unique information that they can provide into the specifics of a process deviation. For example, in some embodiments, the one or more selected features include at least one feature that will fail at the values closest to the nominal values, and the at least one feature has substantially uniform failure across other values of the one or more parameters farther from the nominal values. In this manner, one selected feature may be the process windowing feature in a given region, but may exhibit a substantially uniform failure rate across a broad range of process parameter values.

In one such embodiment, the method includes identifying at least one other of the features that will not fail at the values closest to the nominal values but will fail such that different values of one or more characteristics of the at least one other feature correspond to at least some of the different values of the one or more parameters and selecting the at least one other identified feature as one or more additional features to be used for monitoring the lithography process. In this manner, another feature that is somewhat less prone to failure, and thus is not a PW limiting feature, may provide unique information that would indicate that the process has deviated in a particular direction with a given failure mode. For example, if different values of one or more measurable characteristics of the feature correspond to different values of the one or more parameters, during process control those one or more characteristics of the feature can be measured, and the resulting values can be used to determine the values of the one or more parameters at which the process was operating during printing of the features. Therefore, such a feature type adds important value and is preferably included in the features selected and used for process monitoring.

In another embodiment, the method includes identifying at least one other of the features that will exhibit different types of failure for at least some of the different values of the one or more parameters and selecting the at least one other identified feature as one or more additional features to be used for monitoring the lithography process. For example, selecting the features may be performed to include features that give more information about what process conditions might lead to specific failure types. In one such example, even if the PW feature or features do not include isolated line type features, one or more isolated line type features may be included in the features selected to be used for monitoring the lithography process such that failure types that are specific to isolated lines (e.g., as opposed to dense lines) may be detected during process monitoring.

In some embodiment, the method includes binning the features into groups of lithographically equivalent features. In one such embodiment, selecting the one or more identified features includes selecting at least one feature from each of at least two of the groups such that lithographically unique features are selected as the features to be used for monitoring the lithography process. For example, the method may include binning of lithographically equivalent features to ensure that unique cases are selected. Any appropriate binning technique can be used to combine lithographically equivalent features such as ReviewSmart described in commonly assigned U.S. patent application Ser. No. 10/716,757 by Ma et al. filed Nov. 19, 2003, now U.S. Pat. No. 8,165,384 issued on Apr. 24, 2012, which is incorporated by reference as if fully set forth herein. The embodiments described herein may include any step(s) of any method(s) described in this patent application. In this manner, results of the binning can be used to avoid choosing redundant features for the process control patterns. Choosing lithographically redundant features may be avoided unless one wishes to statistically characterize variations that happen within the process of printing a single wafer.

In one embodiment, the method includes determining an electrical significance of the features. In one such embodiment, identifying the one or more features includes identifying the one or more features as a function of the values closest to the nominal values at which the features will fail and the electrical significance of the features. For example, a control layer can also be included in a manner similar to DesignSmart as described in commonly owned U.S. patent application Ser. No. 11/003,291 by Hess et al. filed Dec. 3, 2004, which published as U.S. Patent Application Publication No. 2006/0051682 on Mar. 9, 2006, now U.S. Pat. No. 8,151,220 issued on Apr. 3, 2010, and which is incorporated by reference as if fully set forth herein, to indicate the relative importance of different features in the design. The embodiments described herein may include any step(s) of any method(s) described in this patent application. In addition, the most electrically significant features may be preferentially used for process control because they are the most relevant. With this control layer, one could weight the relative propensity of a feature to undergo variations and the relative importance of the feature to determine whether it is a useful process control feature.

In some embodiments, the method includes creating a recipe for a metrology tool for monitoring the lithography process based on the one or more selected features. For example, the method may include creating a CD SEM or other metrology tool recipe that will cause that tool to gather the appropriate dimensional or other information from the wafers that have printed from the production process. Ideally, this recipe would be automatically generated and executed, resulting in the automatic collection of data. For example, the method may include generating recipes for a CD SEM tool to gather relevant information for analyzing the results of the CD SEM measurements on the canary features of interest such that the measurements can be used to infer the actual process conditions that caused the deviation from the proper printing of those features. It could, however, be performed with some level of manual intervention. One could either measure every wafer or only some subset of all of the production wafers.

In one embodiment, monitoring the lithography process includes measuring one or more CDs of the one or more selected features using a CD SEM. The CD SEM tool may be configured as described herein. However, any metrology tool can be used for monitoring the lithography process. In other words, the metrology tool is not limited to a CD SEM tool. For example, monitoring the lithography process may include measuring the CDs or other characteristics of the features of interest using the metrology tool. In this manner, the embodiments described herein can form link between a wafer CD SEM tool and a PW microlithography simulation tool such as DesignScan.

In one embodiment, the method includes monitoring the lithography process by measuring one or more characteristics of the one or more selected features printed on wafers by the lithography process and determining deviations in the lithography process based on the one or more characteristics. For example, monitoring the lithography process may include analyzing the results of CD SEM measurements on the canary features of interest and comparing them to the PW lithographic simulation results to infer the actual process conditions that caused the deviation in the proper printing of those features. The ability to infer the actual process deviation allows for the quickest and least expensive correction to the process. This ability can have substantial value to users and has the advantage of spanning existing product lines (e.g., the DesignScan product line and existing CD SEM product lines). The integration of this approach across both of these product lines adds value to both of them.

In another embodiment, the method includes monitoring the lithography process by measuring one or more CDs of the one or more selected features printed on wafers by the lithography process. Deviations in measured values of the one or more CDs from expected values of the one or more CDs indicate deviations in the lithography process. For example, the method may include analyzing the CDs of the measured features to determine if any of them are beginning to deviate from the acceptable range of values. If they do deviate, there is an indication of a potential problem that warrants further analysis, which may be performed as described herein.

In some embodiments, the method includes monitoring the lithography process by measuring one or more characteristics of the one or more selected features printed on wafers by the lithography process and aligning results of the measuring step to results of the simulating step to determine one or more locations on the one or more selected features to be measured by the monitoring. For example, the specific measurement of the CDs may likely require that the simulated results be compared to the measured results no that an alignment can happen to ensure that the proper location on the feature is measured. Comparing the results of the measuring step and the simulating step may be performed as described herein, and aligning the results of the measuring step and the simulating step may be performed as described herein.

In another embodiment, the method includes monitoring the lithography process by measuring one or more characteristics of the one or more selected features printed on wafers by the lithography process, determining deviations in measured values of the one or more characteristics from nominal values of the one or more characteristics, and determining a range of the different values of the one or more parameters that likely caused the variations in the measured values of the one or more characteristics. For example, with the selection of a substantial number of different types of features to monitor, it is likely that multiple different features will start to show variances from nominal CD values if the wafer printing process has started to drift. Analysis of the variations of these different features can indicate what specific process deviation has occurred. For example, if the line width of one feature was smaller than its nominal value, while another was larger than its nominal, one could compare the lithographic simulation results to the measured results to infer the specific process conditions that led to the deviation. In the example above, the first line shrink may indicate that an underexposure has occurred, while the second shrink may indicate that either a negative defocus combined with an underexposure occurred or an overexposure occurred. By combining these results, a range of process parameter values that was likely to have caused the variation may be inferred.

In one embodiment, the method includes monitoring the lithography process by measuring one or more characteristics of the one or more selected features printed on wafers by the lithography process and determining one or more corrective actions to be performed based on the one or more characteristics. For example, the information relating to the process parameter variation, which can be determined according to any of the embodiments described herein, can be fed back into the process to either recalibrate the manufacturing tools, or if one is confident in the results, one can simply adjust the parameter settings (e.g., focus and exposure) to correct the deviation and restore the wafer printing to the proper conditions. Adjusting the parameter settings in such a manner may be performed in any suitable manner known in the art.

The embodiments of the computer-implemented method described above have a number of advantages over other process control features and methods. For example, using all of the design features as the pool from which one selects the process monitoring points provides the broadest range of points and the best indication of a process deviation that can become yield limiting. Using the lithographic simulation to focus on those features that are most prone to failure provides the most efficient use of CD SEM resources and results in the quickest identification of process control problems. In addition, using a relatively large number of different feature regions that have been simulated to be lithographically weak ensures that this technique will select a good representation of points for early detection of different process problems. Also, having several different indicators of problems, multiple indicators can be used to infer the type of process deviation that occurred to create the wafer print variation.

The method may also include using information about defects detected by one or more inspection systems and results of defect review to generate a design for a test structure configured to be monitored for systematic defects and to add the design to a design to be printed on product wafers. For example, the embodiments described herein may be configured for design analysis for "true" automatic defect classification (ADC). Such design analysis may include combining image analysis (e.g., BF, dark field (DF), tilt, etc.), layout, and design and/or process information to perform true ADC. Design analysis may also include secondary analysis such as EDX, FIB, etc. For example, the relatively large amount of information that is available or can be generated as described herein may be used to determine which types of designs or features in designs are most problematic, and those types of designs or features in the designs can be selected as the features to be used for process monitoring purposes.

The embodiments described above may be performed for a design (i.e., a pre-existing design) to select one or more features within the design for process monitoring purposes (thereby also effectively not selecting or de-selecting another one or more features to not be used for process monitoring purposes). However, the monitoring features that are currently placed in the inactive area of the reticle are fairly typical patterns. The patterns are not specifically designed for a specific process or designed to be PW limiting. The patterns also are not specifically designed to sample different portions of PW space.

A different approach to this entire problem would be to design these monitoring features specifically for the manufacturing process to be used. In this manner, the method may use specifically constructed and optimized features in the unused monitoring portion of a design to serve as the canary features described above. This design process may use a lithographic simulation tool such as DesignScan or PRO-LITH, which is also commercially available from KLA-Tencor, to ensure that the features selected and used are PW limiting and can provide unique information about what portion of the PW was used. With this approach, the CD SEM or other monitoring tool can just measure these specific figures and then the same analysis described herein can be applied to determine whether the process was deviating significantly and what the deviation was. A full PW, full chip simulation can then be used to determine whether the process deviation that was detected was being close to being yield limiting.

These problematic types of designs may also be used to create a new test structure or a new test wafer. The test structure or test wafer may include different designs for different processes and may be used to create anew reticle that can be used to print the test structures or the test wafer. The test structures may be positioned at the same location within two or more dies on the wafer, and the two or more dies on the wafer may be spaced across the wafer (e.g., a die near the top of the wafer, a die near the bottom of the wafer, a die near the right side of the wafer, a die near the left side of the wafer, and a die near the center of the wafer). The information for the test structures may also include die location, die design, sample, and PW parameters. The test structure may include the most critical design. For example, such a test structure may be added to an existing product wafer to enable efficient monitoring of systematic defects.

The method may also include using information about defects detected by one or more inspection systems and results of defect review to generate a design for a monitor wafer configured to be monitored for systematic defects after processing of the monitor wafer with product wafers, and the design includes critical designs for the product wafers and variations of the critical designs corresponding to PWs for the critical designs. For example, the monitor wafer may be a full wafer that includes the most critical design and some variations around the PW corresponding to the most critical design that will be monitored. The monitor wafer(s) may be processed together with the remaining product wafers and used to efficiently monitor all possible systematic defects, but also potential random defects. Such processing may be used to prevent the need to inspect and/or review the product wafers as performed traditionally.

Each of the embodiments of the method described above may include any other step(s) of any other method(s) described herein. In addition, the method embodiments described above may include any other step(s) that may be performed by any of the system embodiment(s) described herein. Each of the embodiments of the computer-implemented method described above may be performed by or using any of the system embodiments described herein.

Any of the methods described herein may include storing results of one or more steps of one or more methods described herein in a storage medium. The results may include any of the results described herein. The results may be stored in any manner known in the art. In addition, the storage medium may include any storage medium described herein or any other suitable storage medium known in the art. After the results have been stored, the results can be accessed in the storage medium and used by any of the method or system embodiments described herein or any other method or system. Furthermore, the results may be stored "permanently," "semi-permanently," temporarily, or for some period of time. For example, the storage medium may be random access memory (RAM), and the results may not necessarily persist indefinitely in the storage medium.

Figure 5:
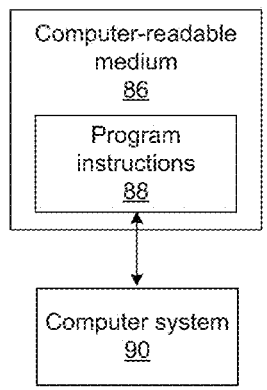
FIG. 5 is a block diagram illustrating one embodiment of a computer-readable medium that includes program instructions executable on a computer system for performing a computer-implemented method for selecting one or more features within a design for use as process monitoring features.

Another embodiment relates to a computer-readable medium that includes program instructions executable on a computer system for performing a computer-implemented method for selecting one or more features within a design for use as process monitoring features. One such embodiment is illustrated in FIG. 5. In particular, as shown in FIG. 5, computer-readable medium 86 includes program instructions 88 executable on computer system 90. The computer-implemented method includes simulating how features in a design will print on a wafer at different values of one or more parameters of a lithography process. Simulating how the features in the design will print may be performed according to any of the embodiments described herein. The different values include nominal values corresponding to a center of a PW of the lithography process. The different values may also include any other values described herein.

The computer-implemented method also includes determining values of the one or more parameters at which the features will fail. Determining the values of the one or more parameters at which the features will fail may be performed according to any of the embodiments described herein. In addition, the computer-implemented method includes identifying one or more of the features that will fail at the values closest to the nominal values. Identifying the one or more features that will fail at the values closest to the nominal values may be performed according to any of the embodiments described herein. The computer-implemented method further includes selecting the one or more identified features as the features to be used for monitoring the lithography process. Selecting the one or more identified features may be performed according to any of the embodiments described herein. The computer-implemented method may include performing any other step(s) of any other embodiment(s) described herein.

Program instructions 88 implementing methods such as those described herein may be stored on computer-readable medium 86. The computer-readable medium may be a computer-readable storage medium such as a read-only memory, a random access memory, a magnetic or optical disk, or a magnetic tape. In addition, the computer-readable medium may include any other suitable computer-readable medium known in the art.

Computer system 90 may take various forms, including a personal computer system, mainframe computer system, workstation, image computer, parallel processor, or any other device known in the art. In general, the term "computer system" may be broadly defined to encompass any device having one or more processors, which executes instructions from a memory medium. In addition, the computer-implemented methods described herein may include using any of the computer systems described herein to perform some or all of the steps of the method.

The computer system described above may be configured as a stand-alone system that does not form part of a process, inspection, metrology, review, or other tool. In such an embodiment, the computer system may be configured to receive and/or acquire data or information from other systems (e.g., inspection results from an inspection system) by a transmission medium that may include "wired" and/or "wireless" portions. In this manner, the transmission medium may serve as a data link between the computer system and the other system. In addition, the computer system may send data to the other system via the transmission medium. Such data may include, for example, results of the methods described herein, inspection recipes or other recipes, or some combination thereof. In other embodiments, however, the computer system is included in a metrology system. The metrology system may be configured as described herein.

Further modifications and alternative embodiments of various aspects of the invention may be apparent to those skilled in the art in view of this description. For example, systems and methods for detecting design and process defects on a wafer, reviewing defects on a wafer, selecting one or more features within a design for use as process monitoring features, or some combination thereof are provided. Accordingly, this description is to be construed as illustrative only and is for the purpose of teaching those skilled in the art the general manner of carrying out the invention, it is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect design and process defects on a wafer, comprising:
    an electron beam review subsystem configured to acquire images for a wafer on a design is printed by a manufacturing process; and
    a computer subsystem configured to:
        inspect the design to detect defects in the design;
        compare an image of a die in the design printed on the wafer acquired by the electron beam review subsystem to an image of the die stored in a database to detect additional defects in the design;
        determine locations on the wafer at which the images are acquired by the electron beam review subsystem based on the defects in the design, the additional defects in the design, and defects detected on the wafer by a wafer inspection system, wherein the electron beam review subsystem acquires images at the locations determined by the computer subsystem;
        detect design defects and process defects at the locations based on the images acquired at the locations by the electron beam review subsystem; and
        compare the images acquired at the locations by the electron beam review subsystem with design clips corresponding to the design defects and the process defects to compare the images to design intent, wherein the design clips are extracted from design data for the design of the wafer, and wherein the design data is generated prior to creation of the wafer for which the images are acquired.

2. The system of claim 1, wherein the computer subsystem is further configured to monitor the design defects and the process defects at the locations on multiple wafers based on the images acquired by the electron beam review subsystem at the locations on the multiple wafers.

3. The system of claim 1, wherein the process defects comprise one of systematic process defects, random process defects, and a combination thereof.

4. The system of claim 1, wherein the computer subsystem is further configured to detect the design defects and the process defects by comparing a portion of the image of the die printed on the wafer to one of the design clips.

5. The system of claim 1, wherein the computer subsystem is further configured to, with the design clips, classify the design defects and the process defects based on locations of the design defects and the process defects in the design, impact of the design defects and the process defects on a process window for the manufacturing process, impact of the design defects and the process defects on functionality of a device corresponding to the design, or some combination thereof.

6. The system of claim 1, wherein the computer subsystem is further configured to identify hot spots in the design and determine the locations on the wafer at which the images are acquired by the electron beam review subsystem based on the hot spots in the design, and wherein the electron beam review subsystem acquires the images at the locations determined by the computer subsystem based on the hot spots.

7. The system of claim 1, wherein the additional defects in the design are not detected by the inspection of the design performed by the computer subsystem.

8. The system of claim 1, wherein the computer subsystem is further configured to detect defects on a reticle by process window qualification analysis and determine the locations on the wafer at which the images are acquired by the electron beam review subsystem based on the defects on the reticle, and wherein the electron beam review subsystem acquires the images at the locations determined by the computer subsystem based on the defects on the reticle.

9. The system of claim 1, wherein the computer subsystem is further configured to determine the locations on the wafer at which the images are acquired by the electron beam review subsystem based on defects detected on a reticle by a reticle inspection system, and wherein the electron beam review subsystem acquires the images at the locations determined by the computer subsystem based on the defects detected on the reticle.

10. The system of claim 1, wherein the computer subsystem is further configured to determine the locations on the wafer at which the images are acquired by the electron beam review subsystem based on yield simulation results, and wherein the electron beam review subsystem acquires the images at the locations determined by the computer subsystem based on the yield simulation results.

11. The system of claim 1, wherein the computer subsystem is further configured to acquire information about the defects detected on the wafer by the wafer inspection system from output generated by the wafer inspection system.

12. The system of claim 1, wherein the electron beam review subsystem is further configured to perform critical dimension measurements at the locations.

13. The system of claim 1, wherein the computer subsystem is further configured to characterize the design defects and the process defects detected at the locations.

14. The system of claim 1, wherein the computer subsystem is further configured to compare the images acquired at the locations by the electron beam review subsystem to the design clips to locate the design defects and the process defects at the locations, classify the design defects and the process defects, perform relative measurements of the design defects and the process defects, and perform marginality analysis of the design defects and the process defects.

15. The system of claim 1, wherein the computer subsystem is further configured to overlay defect information from multiple process steps in the manufacturing process to identify a design and process interaction issue.

16. The system of claim 1, wherein the computer subsystem is further configured to perform marginality analysis by performing differential sizing measurements of the design defects and the process defects to determine if the design defects and the process defects are defects or parametric variations, determine if the design defects and the process defects will impact device performance or reliability, and determine marginality of the parametric variations versus pre-set marginality threshold values.

17. The system of claim 16, wherein the computer subsystem is further configured to perform defect classification based on results of the marginality analysis.

18. The system of claim 16, wherein the pre-set marginality threshold values are determined the electron beam review subsystem.

19. The system of claim 1, wherein the computer subsystem is further configured to alter the design to correct the defects in the design.

20. The system of claim 1, wherein the manufacturing process comprises a lithography process, and wherein the computer subsystem is further configured to monitor a process window of the lithography process based on the images and results of process window qualification analysis performed by an inspection tool.

21. The system of claim 1, wherein the computer subsystem is further configured to determine the locations on the wafer at which the images are acquired by the electron beam review subsystem based on results of inspection of a reticle by a reticle inspection system, wherein the manufacturing process comprises a lithography process performed with the reticle, wherein the electron beam review subsystem acquires the images at the locations determined by the computer subsystem based on the results of the inspection of the reticle, and wherein the computer subsystem is further configured to monitor variations in a process window of the lithography process caused by defects detected on the reticle based on the images and the results of the inspection of the reticle.

22. The system of claim 1, wherein the manufacturing process comprises a lithography process, wherein the computer subsystem is further configured to simulate how features in the design print on the wafer at different values of one or more parameters of the lithography process, wherein the different values comprise nominal values corresponding to a center of a process window of the lithography process, and wherein the computer subsystem is further configured to determine values of the one or more parameters at which the features fail, identify one or more of the features that fail at the values of the one or more parameters closest to the nominal values, and select the one or more identified features as the features for monitoring the lithography process.

23. A system configured to review defects on a wafer, comprising:
an electron beam review subsystem configured to acquire images for discrete locations on a wafer on which a design is printed by a manufacturing process; and a computer subsystem configured to:
  determine the discrete locations based on results of process window qualification analysis;
  perform defect review at the discrete locations based on the images acquired for the discrete locations by the electron beam review subsystem;
  extract images corresponding to the design printed at nominal values of one or more parameters of the manufacturing process from the results of the process window qualification analysis thereby producing extracted images;
  create a recipe for monitoring the discrete locations on multiple wafers based on the extracted images;
  detect design defects and process defects at the discrete locations based on the images acquired at the discrete locations by the electron beam review subsystem; and
  compare the images acquired at the discrete locations by the electron beam review subsystem with design clips corresponding to the design defects and the process defects to compare the images to design intent, wherein the design clips are extracted from design data for the design of the wafer, and wherein the design data is generated prior to creation of the wafer for which the images are acquired.

24. The system of claim 23, wherein the results of the process window qualification analysis comprise defect locations, classification information related to the analysis, and images acquired for the analysis.

25. The system of claim 23, wherein the results of the process window qualification analysis comprise classification information, and wherein the computer subsystem is further configured to, with a file containing the results of the process window qualification analysis, create a recipe for monitoring the discrete locations on multiple wafers.

26. The system of claim 23, wherein the manufacturing process comprises a lithography process, and wherein the computer subsystem is further configured to monitor a process window of the lithography process based on the images acquired for the discrete locations by the electron beam review subsystem and the results of the process window qualification analysis.

27. The system of claim 23, wherein the computer subsystem is further configured to determine the discrete locations based on the results of the process window qualification analysis and results of inspection of a reticle by a reticle inspection system, wherein the manufacturing process comprises a lithography process performed with the reticle, and wherein the computer subsystem is further configured to monitor variations in a process window of the lithography process caused by defects detected on the reticle based on the images and the results of the inspection of the reticle.

28. The system of claim 23, wherein the process window qualification analysis is performed by an inspection system.

29. The system of claim 23, wherein the electron beam review subsystem comprises an optical microscope, wherein the computer subsystem is further configured to identify the discrete locations on the wafer based on images for the discrete locations acquired by the optical microscope and optical patch images for the discrete locations acquired by a wafer inspection system, and wherein the system is further configured to position the discrete locations in a field of view of the electron beam review subsystem based on the identified discrete locations.

30. The system of claim 23, wherein the computer subsystem is further configured to determine if defects exist at the discrete locations based on the images acquired for the discrete locations by the electron beam review subsystem.

31. The system of claim 23, wherein the results of the process window qualification analysis comprise Bossung images, and wherein the computer subsystem is further configured to perform the defect review at the discrete locations by comparing the Bossung images to the images acquired for the discrete locations by the electron beam review subsystem.

32. The system of claim 23, wherein the computer subsystem is further configured to import the results of the process window qualification analysis from a system that performed the process window qualification analysis.

33. The system of claim 23, wherein the computer subsystem is further configured to determine the discrete locations based on the results of the process window qualification analysis, defects in the design detected by inspection of the design, additional defects in the design detected by comparing an image of a die in the design printed on the wafer to an image of the die stored in a database, and defects detected on the wafer by a wafer inspection system.

34. The system of claim 23, wherein the manufacturing process comprises a lithography process, wherein the computer subsystem is further configured to simulate how features in the design print on the wafer at different values of one or more parameters of the lithography process, wherein the different values comprise nominal values corresponding to a center of a process window of the lithography process, and wherein the computer subsystem is further configured to determine values of the one or more parameters at which the features fail, identify one or more of the features that fail at the values closest to the nominal values, and select the one or more identified features as the features for monitoring the lithography process.

35. A system configured to review defects on a wafer, comprising:
  an electron beam review subsystem configured to acquire images for discrete locations on a wafer on which a design is printed by a lithography process performed with a reticle; and
  a computer subsystem configured to determine the discrete locations based on results of inspection of the reticle, to perform defect review at the discrete locations based on the images acquired for the discrete locations by the electron beam review subsystem, the results of the inspection of the reticle, and classification of defects detected on the reticle, and to compare the images acquired for the discrete locations by the electron beam review subsystem with design clips corresponding to the defects to compare the images to design intent, wherein the design clips are extracted from design data for the design of the wafer, and wherein the design data is generated prior to creation of the wafer for which the images are acquired.

36. The system of claim 35, wherein the computer subsystem is further configured to monitor variations in a process window of the lithography process caused by the defects detected on the reticle based on the results of the inspection of the reticle and the images acquired for the discrete locations by the electron beam review subsystem.

37. The system of claim 35, wherein the classification of the defects detected on the reticle is performed by a reticle inspection system.

38. The system of claim 35, wherein the discrete locations comprise discrete locations of the detects that affect a process window of the lithography process, discrete locations of the detects that do not affect the process window, discrete locations of the defects that print on the wafer, and discrete locations of the defects that do not print on the wafer such that all marginal defects on the reticle are reviewed and captured.

39. The system of claim 35, wherein the discrete locations comprise discrete locations of defects having a size that renders them undetectable by a bright field optical wafer inspection system, and wherein the computer subsystem is further configured to perform differential sizing analysis of the detects that are undetectable by the bright field optical wafer inspection system.

40. The system of claim 35, wherein the computer subsystem is further configured to perform differential sizing analysis of defects at the discrete locations by comparing feature dimensions in the images acquired for the discrete locations by the electron beam review subsystem to dimensions of neighboring features in the same die as the discrete locations.

41. The system of claim 35, wherein the computer subsystem is further configured to acquire a file from a reticle inspection system, wherein the file comprises the results of the inspection of the reticle, design coordinates, and the design clips, and wherein the computer subsystem is further configured to translate reticle coordinates into wafer coordinates based on the results of the inspection of the reticle, the design coordinates, and the design clips.

42. The system of claim 35, wherein the computer subsystem is further configured to position the discrete locations in a field of view of the electron beam review subsystem based on the design clips corresponding to the defects.

43. The system of claim 35, wherein the computer subsystem is further configured to append the images acquired for the discrete locations by the electron beam review subsystem to a file comprising the results of the inspection of the reticle, and wherein a reticle inspection system is configured to setup a recipe for reticle inspection based on the images appended to the file by the computer subsystem.

44. The system of claim 35, wherein the computer subsystem is further configured to append the images acquired for the discrete locations by the electron beam review subsystem to a file comprising the results of the inspection of the reticle, and wherein a computer-implemented method comprises setting up a recipe for inspection of an additional design based on the images appended to the file by the computer subsystem.

45. The system of claim 35, wherein the computer subsystem is further configured to alter a recipe for inspection of reticles based on results of the detect review at the discrete locations.

46. The system of claim 35, wherein the computer subsystem is coupled to a reticle inspection system such that the computer subsystem sends information to the reticle inspection system and receives information from the reticle inspection system.

47. The system of claim 35, wherein the computer subsystem is further configured to compare the images acquired for the discrete locations to images of a die stored in a database.

48. The system of claim 35, wherein the computer subsystem is further configured to determine the discrete locations based on the results of the inspection of the reticle, defects in the design detected by inspection of the design, additional defects in the design detected by comparing an image of a die in the design printed on the wafer to an image of the die stored in a database, and defects detected on the wafer by a wafer inspection system.

49. The system of claim 35, wherein the computer subsystem is further configured to determine the discrete locations based on the results of the inspection of the reticle and results of process window qualification analysis performed for the reticle.

50. The system of claim 35, wherein the computer subsystem is further configured to simulate how features in the design print on the wafer at different values of one or more parameters of the lithography process, wherein the different values comprise nominal values corresponding to a center of a process window of the lithography process, and wherein the computer subsystem is further configured to determine values of the one or more parameters at which the features fail, identify one or more of the features that fail at the values closest to the nominal values, and select the one or more identified features as the features for monitoring the lithography process.

\* \* \* \* \*